(12) United States Patent
Simpson et al.

(10) Patent No.: US 10,335,173 B2
(45) Date of Patent: Jul. 2, 2019

(54) RE-ENTRY STYLET FOR CATHETER

(71) Applicant: Avinger, Inc., Redwood City, CA (US)

(72) Inventors: John B. Simpson, Woodside, CA (US);
Myra L. Fabro, San Jose, CA (US);
Eduardo Sucgang, South San Francisco, CA (US); Priyanshu Gupta, Palo Alto, CA (US); Theodore W. Ketai, San Francisco, CA (US)

(73) Assignee: Avinger, Inc., Redwood City, CA (US)

( * ) Notice: Subject to any disclaimer, the term of this patent is extended or adjusted under 35 U.S.C. 154(b) by 629 days.

(21) Appl. No.: 14/424,266

(22) PCT Filed: Mar. 15, 2013

(86) PCT No.: PCT/US2013/032196
§ 371 (c)(1),
(2) Date: Feb. 26, 2015

(87) PCT Pub. No.: WO2015/039096
PCT Pub. Date: Mar. 13, 2014

(65) Prior Publication Data
US 2015/0320975 A1 Nov. 12, 2015

Related U.S. Application Data

(60) Provisional application No. 61/697,726, filed on Sep. 6, 2012.

(51) Int. Cl.
*A61M 25/00* (2006.01)
*A61M 25/01* (2006.01)
*A61B 17/22* (2006.01)

(52) U.S. Cl.
CPC ......... *A61B 17/22* (2013.01); *A61M 25/0041* (2013.01); *A61M 25/0102* (2013.01);
(Continued)

(58) Field of Classification Search
CPC .......... A61M 25/0041; A61M 25/0102; A61M 25/0194
(Continued)

(56) References Cited

U.S. PATENT DOCUMENTS 3,908,637 A * 9/1975 Doroshow ............... A61B 1/12
600/550
4,178,935 A 12/1979 Gekhaman et al.
(Continued)

FOREIGN PATENT DOCUMENTS

CN 1875242 A 12/2006
CN 1947652 A 4/2007
(Continued)

OTHER PUBLICATIONS

Gupta et al.; U.S. Appl. No. 14/776,749 entitled "Tissue collection device for catheter," filed Sep. 15, 2015.
(Continued)

*Primary Examiner* — Edelmira Bosques
(74) *Attorney, Agent, or Firm* — Shay Glenn LLP

(57) ABSTRACT

A stylet for re-entry into a vessel includes an elongate body including a proximal portion, a middle curved portion, a pointed distal end, and a longitudinal axis extending through the proximal portion, the middle curved portion, and the pointed distal end. The proximal portion and the middle curved portion have substantially circular cross-sections. The middle curved portion has a pre-shaped curve along the longitudinal axis configured to match a curve of an occlusion-crossing device. The pointed distal end has an s-curve along the longitudinal axis and a flattened portion along the longitudinal axis, the flattened portion having a substantially oblong cross-section.

17 Claims, 17 Drawing Sheets

(52) U.S. Cl.
CPC ............... *A61M 25/0194* (2013.01); *A61B 2017/22095* (2013.01); *A61M 2025/0197* (2013.01)

(58) Field of Classification Search
USPC .................................................. 604/510
See application file for complete search history.

(56) References Cited

U.S. PATENT DOCUMENTS

| | | | |
|---|---|---|---|
| 4,487,206 A | 12/1984 | Aagard | |
| 4,527,553 A | 7/1985 | Upsher | |
| 4,552,554 A | 11/1985 | Gould et al. | |
| 4,621,353 A | 11/1986 | Hazel et al. | |
| 4,639,091 A | 1/1987 | Huignard et al. | |
| 4,654,024 A | 3/1987 | Crittenden et al. | |
| 4,686,982 A | 8/1987 | Nash | |
| 4,691,708 A | 9/1987 | Kane | |
| 4,771,774 A | 9/1988 | Simpson et al. | |
| 4,841,977 A | 6/1989 | Griffith et al. | |
| 4,857,046 A | 8/1989 | Stevens et al. | |
| 4,920,961 A | 5/1990 | Grossi et al. | |
| 4,926,858 A | 5/1990 | Gifford, III et al. | |
| 5,000,185 A | 3/1991 | Yock | |
| 5,018,529 A | 5/1991 | Tenerz et al. | |
| 5,041,082 A | 8/1991 | Shiber | |
| 5,047,040 A | 9/1991 | Simpson et al. | |
| 5,085,662 A | 2/1992 | Willard | |
| 5,099,850 A | 3/1992 | Matsui et al. | |
| 5,178,153 A | 1/1993 | Einzig | |
| 5,182,291 A | 1/1993 | Gubin et al. | |
| 5,190,050 A | 3/1993 | Nitzsche | |
| 5,192,291 A | 3/1993 | Pannek, Jr. | |
| 5,312,415 A | 5/1994 | Palermo | |
| 5,312,425 A | 5/1994 | Evans et al. | |
| 5,321,501 A | 6/1994 | Swanson et al. | |
| 5,333,142 A | 7/1994 | Scheps | |
| 5,358,472 A | 10/1994 | Vance et al. | |
| 5,366,464 A | 11/1994 | Belknap | |
| 5,383,460 A | 1/1995 | Jang et al. | |
| 5,383,467 A | 1/1995 | Auer et al. | |
| 5,425,273 A | 6/1995 | Chevalier | |
| 5,429,136 A | 7/1995 | Milo et al. | |
| 5,431,673 A | 7/1995 | Summers et al. | |
| 5,437,284 A | 8/1995 | Trimble | |
| 5,459,570 A | 10/1995 | Swanson et al. | |
| 5,460,168 A | 10/1995 | Masubuchi et al. | |
| 5,465,147 A | 11/1995 | Swanson | |
| 5,507,795 A | 4/1996 | Chiang et al. | |
| 5,556,405 A | 9/1996 | Lary | |
| 5,607,394 A * | 3/1997 | Andersen | A61M 25/104 604/102.01 |
| 5,620,426 A | 4/1997 | Braithwaite | |
| 5,632,754 A | 5/1997 | Farley et al. | |
| 5,632,755 A | 5/1997 | Nordgren et al. | |
| 5,674,232 A | 10/1997 | Halliburton | |
| 5,681,336 A | 10/1997 | Clement et al. | |
| 5,690,634 A | 11/1997 | Muller et al. | |
| 5,722,403 A | 3/1998 | McGee et al. | |
| 5,728,148 A * | 3/1998 | Bostrom | A61N 1/056 600/373 |
| 5,795,295 A | 8/1998 | Hellmuth et al. | |
| 5,807,339 A | 9/1998 | Bostrom et al. | |
| 5,830,145 A | 11/1998 | Tenhoff | |
| 5,836,957 A | 11/1998 | Schulz et al. | |
| 5,843,050 A | 12/1998 | Jones et al. | |
| 5,843,103 A | 12/1998 | Wulfman | |
| 5,868,778 A | 2/1999 | Gershony et al. | |
| 5,872,879 A | 2/1999 | Hamm | |
| 5,904,651 A | 5/1999 | Swanson et al. | |
| 5,907,425 A | 5/1999 | Dickensheets et al. | |
| 5,935,075 A | 8/1999 | Casscells et al. | |
| 5,938,602 A | 8/1999 | Lloyd | |
| 5,951,482 A | 9/1999 | Winston et al. | |
| 5,951,581 A | 9/1999 | Saadat et al. | |
| 5,951,583 A | 9/1999 | Jensen et al. | |
| 5,956,355 A | 9/1999 | Swanson et al. | |
| 5,957,952 A | 9/1999 | Gershony et al. | |
| 5,987,995 A | 11/1999 | Sawatari et al. | |
| 5,997,558 A | 12/1999 | Nash | |
| 6,001,112 A | 12/1999 | Taylor | |
| 6,007,530 A | 12/1999 | Dornhofer et al. | |
| 6,010,449 A | 1/2000 | Selmon et al. | |
| 6,013,072 A | 1/2000 | Winston et al. | |
| 6,017,359 A | 1/2000 | Gershony et al. | |
| 6,027,514 A | 2/2000 | Stine et al. | |
| 6,032,673 A | 3/2000 | Savage et al. | |
| 6,048,349 A | 4/2000 | Winston et al. | |
| 6,080,170 A | 6/2000 | Nash et al. | |
| 6,106,515 A | 8/2000 | Winston et al. | |
| 6,110,164 A | 8/2000 | Vidlund | |
| 6,120,515 A | 9/2000 | Rogers et al. | |
| 6,120,516 A | 9/2000 | Selmon et al. | |
| 6,134,002 A | 10/2000 | Stimson et al. | |
| 6,134,003 A | 10/2000 | Tearney et al. | |
| 6,152,938 A | 11/2000 | Curry | |
| 6,152,951 A | 11/2000 | Hashimoto et al. | |
| 6,160,826 A | 12/2000 | Swanson et al. | |
| 6,175,669 B1 | 1/2001 | Colston et al. | |
| 6,176,871 B1 | 1/2001 | Pathak et al. | |
| 6,183,432 B1 | 2/2001 | Milo | |
| 6,193,676 B1 | 2/2001 | Winston et al. | |
| 6,206,898 B1 | 3/2001 | Honeycutt et al. | |
| 6,228,076 B1 | 5/2001 | Winston et al. | |
| 6,241,744 B1 | 6/2001 | Imran et al. | |
| 6,283,957 B1 | 9/2001 | Hashimoto et al. | |
| 6,290,668 B1 | 9/2001 | Gregory et al. | |
| 6,294,775 B1 | 9/2001 | Seibel et al. | |
| 6,299,622 B1 | 10/2001 | Snow et al. | |
| 6,307,985 B1 | 10/2001 | Murakami et al. | |
| 6,402,719 B1 | 6/2002 | Ponzi et al. | |
| 6,416,527 B1 | 7/2002 | Berg et al. | |
| 6,445,939 B1 | 9/2002 | Swanson et al. | |
| 6,445,944 B1 | 9/2002 | Ostrovsky | |
| 6,447,525 B2 | 9/2002 | Follmer et al. | |
| 6,451,036 B1 | 9/2002 | Heitzmann et al. | |
| 6,454,717 B1 | 9/2002 | Pantages et al. | |
| 6,454,779 B1 | 9/2002 | Taylor | |
| 6,482,216 B1 | 11/2002 | Hiblar et al. | |
| 6,482,217 B1 | 11/2002 | Pintor et al. | |
| 6,485,413 B1 | 11/2002 | Boppart et al. | |
| 6,497,649 B2 | 12/2002 | Parker et al. | |
| 6,501,551 B1 | 12/2002 | Tearney et al. | |
| 6,503,261 B1 | 1/2003 | Bruneau et al. | |
| 6,511,458 B2 | 1/2003 | Milo et al. | |
| 6,517,528 B1 | 2/2003 | Pantages et al. | |
| 6,542,665 B2 | 4/2003 | Reed et al. | |
| 6,546,272 B1 | 4/2003 | MacKinnon et al. | |
| 6,551,302 B1 | 4/2003 | Rosinko et al. | |
| 6,563,105 B2 | 5/2003 | Seibel et al. | |
| 6,564,087 B1 | 5/2003 | Pitris et al. | |
| 6,565,588 B1 | 5/2003 | Clement et al. | |
| 6,572,563 B2 | 6/2003 | Ouchi et al. | |
| 6,572,643 B1 | 6/2003 | Gharibadeh | |
| 6,575,995 B1 | 6/2003 | Huter et al. | |
| 6,579,298 B1 | 6/2003 | Bruneau et al. | |
| 6,615,071 B1 | 9/2003 | Casscells, III et al. | |
| 6,638,233 B2 | 10/2003 | Corvi et al. | |
| 6,645,217 B1 | 11/2003 | MacKinnon et al. | |
| 6,657,727 B1 | 12/2003 | Izatt et al. | |
| 6,666,874 B2 | 12/2003 | Heitzmann et al. | |
| 6,687,010 B1 | 2/2004 | Horii | |
| 6,728,571 B1 | 4/2004 | Barbet | |
| D489,973 S | 5/2004 | Root et al. | |
| 6,730,063 B2 | 5/2004 | Delaney et al. | |
| 6,758,854 B1 | 7/2004 | Butler et al. | |
| 6,760,112 B2 | 7/2004 | Reed et al. | |
| 6,800,085 B2 | 10/2004 | Selmon et al. | |
| 6,818,001 B2 | 11/2004 | Wulfman et al. | |
| 6,824,550 B1 | 11/2004 | Noriega et al. | |
| 6,830,577 B2 | 12/2004 | Nash et al. | |
| 6,845,190 B1 | 1/2005 | Smithwick et al. | |
| 6,852,109 B2 | 2/2005 | Winston et al. | |
| 6,853,457 B2 | 2/2005 | Bjarklev et al. | |

(56) References Cited

U.S. PATENT DOCUMENTS

| | | |
|---|---|---|
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,068,921 B2 * | 11/2011 | Prakash ............. A61B 18/18 606/101 |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,696,695 B2 | 4/2014 | Patel et al. |
| 8,911,459 B2 | 12/2014 | Simpson et al. |
| 9,119,662 B2 | 9/2015 | Moberg |
| 9,351,757 B2 | 5/2016 | Kusleika |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0075660 A1 * | 4/2005 | Chu ............. A61B 17/06109 606/190 |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 * | 10/2006 | Arnal ............. A61B 17/06066 600/30 |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |

(56) References Cited

U.S. PATENT DOCUMENTS

| | | |
|---|---|---|
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0078469 A1 | 4/2007 | Soito et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0080016 A1 | 4/2010 | Fukui et al. |
| 2010/0125253 A1 | 5/2010 | Olson |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0004107 A1 | 1/2011 | Rosenthal et al. |
| 2011/0021926 A1 | 1/2011 | Spencer et al. |
| 2011/0023617 A1 | 2/2011 | Miao et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0046679 A1 | 2/2012 | Patel et al. |
| 2012/0123352 A1 | 5/2012 | Fruland et al. |
| 2012/0238869 A1 | 9/2012 | Schmitt et al. |
| 2012/0259337 A1 | 10/2012 | del Rio et al. |
| 2012/0289971 A1 | 11/2012 | Segermark et al. |
| 2013/0035692 A1 | 2/2013 | Sorensen et al. |
| 2013/0096589 A1 | 4/2013 | Spencer et al. |
| 2013/0123615 A1 | 5/2013 | Spencer et al. |
| 2013/0138128 A1 | 5/2013 | Patel et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0289392 A1 | 10/2013 | Patel et al. |
| 2013/0296695 A1 | 11/2013 | Spencer et al. |
| 2013/0317519 A1 | 11/2013 | Romo et al. |
| 2014/0005534 A1 | 1/2014 | He et al. |
| 2014/0128893 A1 | 5/2014 | Guggenheimer et al. |
| 2014/0187949 A1 | 7/2014 | Zhao et al. |
| 2014/0213893 A1 | 7/2014 | Simpson et al. |
| 2014/0222047 A1 | 8/2014 | Vreeman |
| 2014/0371718 A1 | 12/2014 | Alvarez et al. |
| 2015/0025310 A1 | 1/2015 | Everingham et al. |
| 2015/0099984 A1 | 4/2015 | Kankaria |
| 2015/0126856 A1 | 5/2015 | Tachibana et al. |
| 2015/0164530 A1 | 6/2015 | Carver et al. |
| 2015/0208922 A1 | 7/2015 | Newhauser et al. |
| 2016/0192962 A1 | 7/2016 | Simpson et al. |
| 2016/0199092 A1 | 7/2016 | Patel et al. |
| 2018/0256187 A1 | 9/2018 | Patel et al. |

FOREIGN PATENT DOCUMENTS

| | | |
|---|---|---|
| CN | 101601581 A | 12/2009 |
| CN | 103027727 A | 4/2013 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |

(56) References Cited

FOREIGN PATENT DOCUMENTS

| | | |
|---|---|---|
| JP | S62-275425 A | 11/1987 |
| JP | 03502060 A | 2/1990 |
| JP | 05103763 A | 4/1993 |
| JP | H06-027343 A | 2/1994 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2005-533533 A | 11/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |
| JP | 2007-83053 A | 4/2007 |
| JP | 2007-83057 A | 4/2007 |
| JP | 2007-225349 A | 9/2007 |
| JP | 2007533361 A | 11/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-66252 A | 4/2009 |
| JP | 2009-78150 A | 4/2009 |
| JP | 2010042182 A | 2/2010 |
| JP | 2010518900 A | 6/2010 |
| JP | 2011521747 A | 7/2011 |
| JP | 2012533353 A | 12/2012 |
| JP | 2016508758 A | 3/2016 |
| KR | 2007/0047221 | 5/2007 |
| RU | 2185859 C2 | 7/2002 |
| RU | 2218191 C2 | 12/2003 |
| WO | WO 91/17698 A1 | 11/1991 |
| WO | WO 99/23958 A1 | 5/1999 |
| WO | WO 00/54659 A1 | 9/2000 |
| WO | WO01/15609 A1 | 3/2001 |
| WO | WO 01/76680 A1 | 10/2001 |
| WO | WO 2006/133030 A2 | 12/2006 |
| WO | WO2008/005888 A2 | 1/2008 |
| WO | WO 2008/029506 A | 3/2008 |
| WO | WO 2008/042987 A2 | 4/2008 |
| WO | WO2008/051951 A1 | 5/2008 |
| WO | WO 2008/065600 A2 | 6/2008 |
| WO | WO 2008/086613 A1 | 7/2008 |
| WO | WO 2008/087613 A2 | 7/2008 |
| WO | WO2009/005779 A1 | 1/2009 |
| WO | WO2009/006335 A1 | 1/2009 |
| WO | WO 2009/009799 A1 | 1/2009 |
| WO | WO2009/009802 A1 | 1/2009 |
| WO | WO 2009/023635 A | 2/2009 |
| WO | WO2009/024344 A1 | 2/2009 |
| WO | WO 2009/094341 A2 | 7/2009 |
| WO | WO 2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO 2012/061935 A1 | 5/2012 |
| WO | WO2012/166332 A1 | 12/2012 |
| WO | WO2013/033490 A1 | 3/2013 |
| WO | WO2013/056262 A1 | 4/2013 |

OTHER PUBLICATIONS

Smith et al.; U.S. Appl. No. 14/776,750 entitled "Chronic total occlusion crossing devices with imaging," filed Sep. 15, 2015.
Smith et al.; U.S. Appl. No. 14/776,748 entitled "Optical pressure sensor assembly," filed Sep. 15, 2015.
Simpson et al.; U.S. Appl. No. 14/899,877 entitled "Occusion sheath for imaging catheter," filed Dec. 18, 2015.
Simpson et al.; U.S. Appl. No. 14/899,893 entitled "Identification of elastic lamina to guide interventional therapy," filed Dec. 18, 2015.
Patel et al.; U.S. Appl. No. 15/162,330 entitled "Atherectomy catheters with longitudinally displaceable drive shafts," filed May 23, 2016.
Spencer et al.; U.S. Appl. No. 15/162,353 entitled "Occlusion-crossing devices, atherectomy devices, and imaging," filed May 23, 2016.
Tachibana et al.; U.S. Appl. No. 15/162,391 entitled "Atherectomy catheter drive assemblies," filed May 23, 2016.
Rosenthal et al.; U.S. Appl. No. 15/354,898 entitled "Atherectomy catheter with laterally-displaceable tip," filed Nov. 17, 2017.
Patel et al.; U.S. Appl. No. 15/354,842 entitled "Atherectomy catheters and occlusion crossing devices," filed Nov. 17, 2016.
Shinkle et al.; Evaluation of stent placement and outcomes with optical coherence tomography; Interv. Cardiol.; 2(4); pp. 535-543; (manuscript version, 12 pages); Aug. 2010.
Patel et al.; U.S. Appl. No. 15/324,325 entitled "High speed chronic total occulusion crossing devices," filed Jan. 6, 2017.
Kankaria; U.S. Appl. No. 15/419,815 entitled "Optical coherence tomography with graded index fiber for biological imaging," filed Jan. 30, 2017.
Simpson et al.; U.S. Appl. No. 15/434,758 entitled "Occlusion-crossing devices, imaging, and atherectomy devices," filed Feb. 16, 2017.
Simpson et al.; U.S. Appl. No. 15/457,960 entitled "Atherectomy catheters devices having multi-channel bushings," filed Mar. 13, 2017.
Patel et al.; U.S. Appl. No. 15/480,238 entitled "Guidewire positioning catheter," filed Apr. 5, 2017.
Black et al.; U.S. Appl. No. 15/783,800 entitled "Optical coherence tomography for biological imaging," filed Oct. 13, 2017.
Gupta et al.; U.S. Appl. No. 14/401,175 entitled "Atherectomy catheters with imaging," filed Nov. 14, 2014.
Simpson et al.; U.S. Appl. No. 14/424,277 entitled "Balloon atherectomy catheters with imaging," filed Feb. 26, 2015.
Aziz et al.; Chronic total occlusions—a stiff challenge requiring a major breakthrough: is there light at the end of the tunnel?; Heart; vol. 91; suppl. III; pp. 42-48; Jun. 2005.
Emkey et al.; Analysis and evaluation of graded-index fiber-lenses; Journal of Lightwave Technology; vol. LT-5; No. 9; pp. 1156-1164; Sep. 1987.
Gonzalo et al.; Optical coherence tomography patterns of stent restenosis; Am. Heart J.; 158(2); pp. 284-293; Aug. 2009.
Linares et al.; Arbitrary single-mode coupling by tapered and nontapered grin fiber lenses; Applied Optics; vol. 29; No. 28; pp. 4003-4007; Oct. 1, 1990.
Sharma et al.; Optical coherence tomography based on an all-fiber autocorrelator using probe-end reflection as reference; CWJ13; San Francisco, California; CLEO May 16, 2004; 4 pages.
Suparno et al.; Light scattering with single-mode fiber collimators; Applied Optics; vol. 33; No. 30; pp. 7200-7205; Oct. 20, 1994.
Han et al.; In situ Frog Retina Imaging Using Common-Path OCT with a Gold-Coated Bare Fiber Probe; CFM6; San Jose, California; CLEO, May 4, 2008; 2 pages.
Muller et al.; Time-gated infrared fourier-domain optical coherence tomography; CFM5; San Jose, California; CLEO May 4, 2008; 2 pages.
Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.
Wang et al.; Common-path endoscopic Fourier domain OCT with a reference Michelson interferometer; Proceedings of the SPIE; vol. 7566; pp. 75660L-75660L-7; Jan. 2010.
Smith et al.; U.S. Appl. No. 15/854,579 entitled "Chronic total occusion crossing devices with imaging," filed Dec. 26, 2017.
Patel et al.; U.S. Appl. No. 15/741,928 entitled "Micro-molded anamorpjic reflector lens for image guided therapeutic/diagnostic catheters," filed Jan. 4, 2018.

(56) References Cited

OTHER PUBLICATIONS

Zung et al.; U.S. Appl. No. 15/741,773 entitled "Self-alignment mechanism for imaging cather and drive assembly," filed Jan. 4, 2018.
Newhauser et al.; U.S. Appl. No. 15/954,407 entitled "Occlusion-crossing devices," filed Apr. 16, 2018.
Christensen; U.S. Appl. No. 16/069,545 entitled "OCT imaging catheter with lag correction," filed Jul. 12, 2018.
Rosenthal et al.; U.S. Appl. No. 16/105,743 entitled "Atherectomy catheter with laterally-displaceable tip," filed Aug. 20, 2018.
Patel et al.; U.S. Appl. No. 16/148,246 entitled "Atherectomy catheter with serrated cutter," filed Oct. 1, 2018.

\* cited by examiner

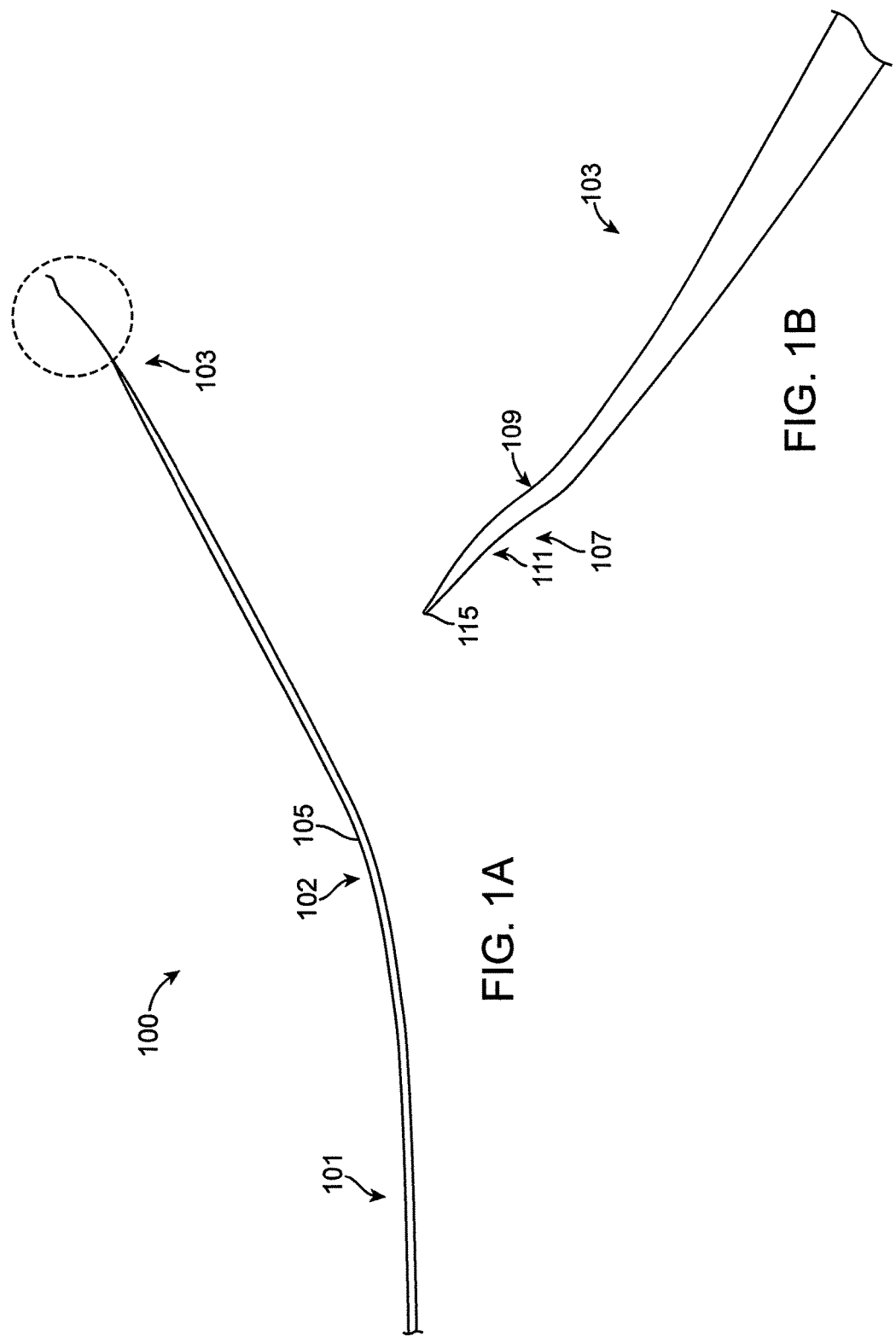

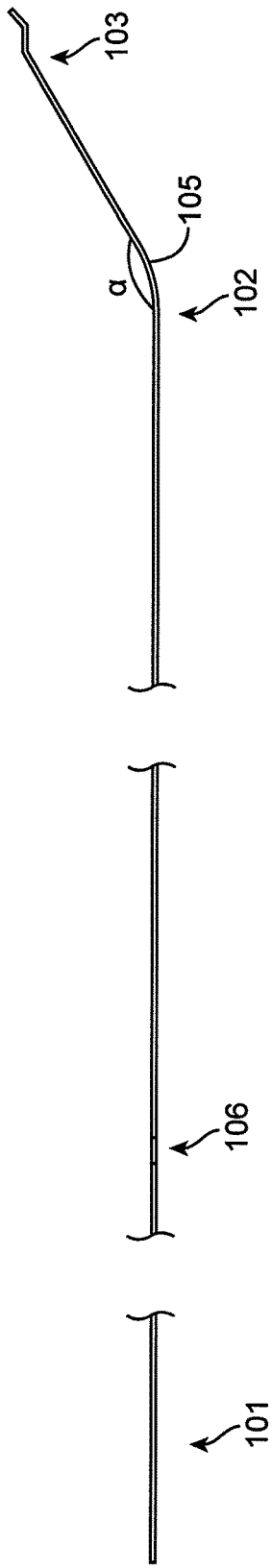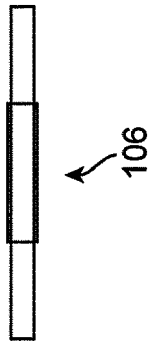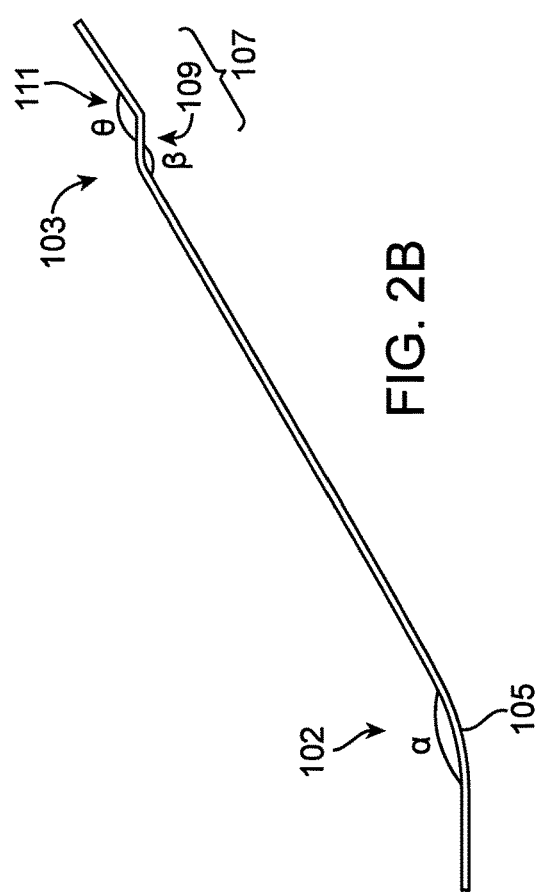
FIG. 2A
FIG. 2C
FIG. 2B

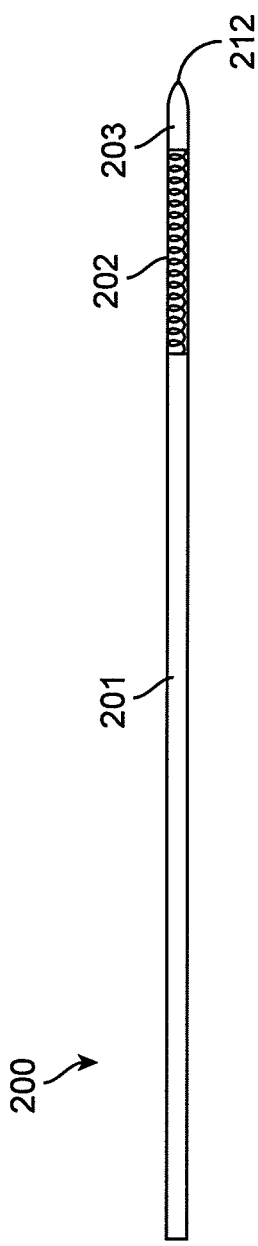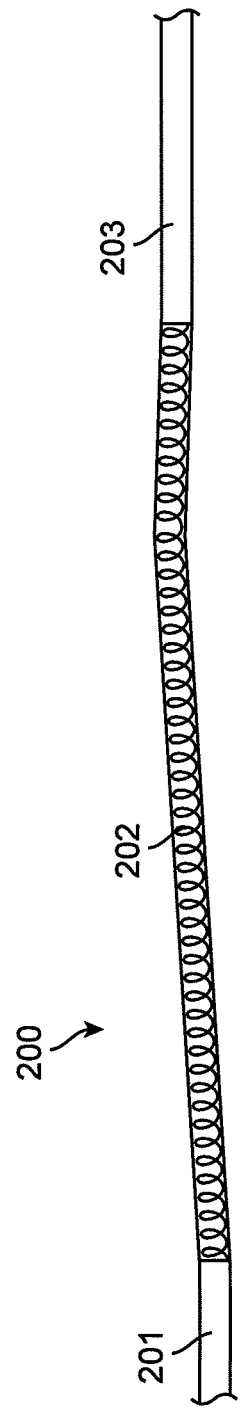
FIG. 3A
FIG. 3B

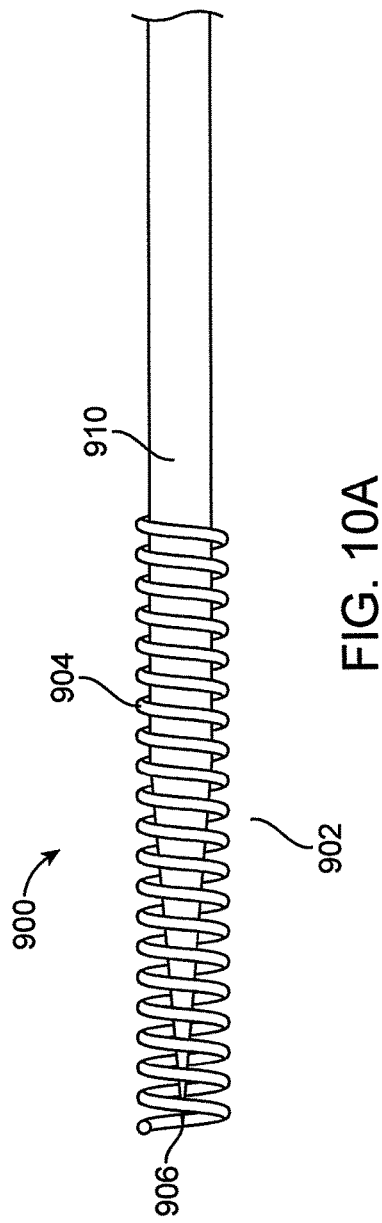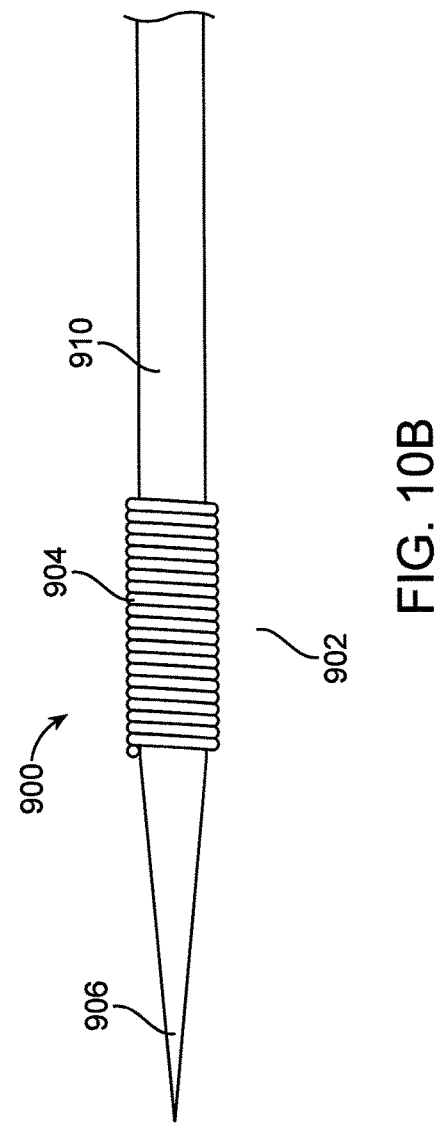
FIG. 10A
FIG. 10B

RE-ENTRY STYLET FOR CATHETER

CROSS REFERENCE TO RELATED APPLICATION

This application claims the benefit of U.S. Provisional Patent Application No. 61/697,726, filed Sep. 6, 2012, and titled "RE-ENTRY STYLET FOR CATHETER," which is herein incorporated by reference in its entirety.

INCORPORATION BY REFERENCE

All publications and patent applications mentioned in this specification are herein incorporated by reference in their entireties to the same extent as if each individual publication or patent application was specifically and individually indicated to be incorporated by reference.

BACKGROUND

Peripheral artery disease (PAD) affects millions of people in the United States alone. PAD is a dangerous disease that can have catastrophic consequences when left untreated. PAD is the leading cause of amputation in patients over 50 and is responsible for approximately 160,000 amputations in the United States each year.

Peripheral artery disease (PAD) is a progressive narrowing of the blood vessels most often caused by atherosclerosis, the collection of plaque or a fatty substance along the inner lining of the artery wall. Over time, this substance hardens and thickens, which may interfere with blood circulation to the arms, legs, stomach and kidneys. This narrowing forms an occlusion, completely or partially restricting flow through the artery. The most significant of these occlusions are called chronic total occlusions (CTO). Blood circulation to the brain and heart may be reduced by CTOs, increasing the risk for stroke and heart disease.

Interventional treatments for PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and is positioned such that the balloon resides within the blockage. The balloon, connected to the catheter, is expanded to open the artery. Surgeons may then place a wire mesh tube, called a stent, at the area of blockage to keep the artery open.

Such minimally invasive techniques (e.g., atherectomy, angioplasty, etc.) typically involve the placement of a guidewire through the occlusion. Using the guidewire, one or more interventional devices may be positioned to remove or displace the occlusion. Unfortunately, placement of the guidewire, while critical for effective treatment, may be difficult. In particular, when placing a guidewire across an occlusion, it may be difficult to pass the guidewire through the occlusion while avoiding damage to the artery. For example, it is often difficult to prevent the guidewire from traveling out of the true lumen and into the subintimal layers, such as the adventitia and surrounding tissues. This can cause damage to the vessel and, once out of the true lumen, it can be difficult to direct the guidewire back into the true lumen, thereby preventing effective treatment of the occlusion.

Accordingly, a device for effectively crossing an occlusion and/or for reentering the true lumen after entering the subintimal layers would be beneficial.

SUMMARY OF THE DISCLOSURE

The present invention relates generally to stylets, and more specifically to stylets used to cross occlusions and/or to re-enter a true lumen of a vessel.

In general, in one embodiment, a stylet for re-entry into a vessel includes an elongate body including a proximal portion, a middle curved portion, a pointed distal end, and a longitudinal axis extending through the proximal portion, the middle curved portion, and the pointed distal end. The proximal portion and the middle curved portion have substantially circular cross-sections. The middle curved portion has a pre-shaped curve along the longitudinal axis configured to match a curve of an occlusion-crossing device. The pointed distal end has an s-curve along the longitudinal axis and a flattened portion along the longitudinal axis, the flattened portion having a substantially oblong cross-section.

This and other embodiments can include one or more of the following features. The s-curve can be within the flattened portion. At least one of the distal end or the middle curved portion can include nitinol. The proximal portion can include stainless steel. The pre-shaped curve can form an angle of 130 to 170 degrees. The angle can be approximately 150 degrees. The s-shaped curve can have two curves, the first curve can form a first angle of 120 to 160 degrees and the second curve can form an angle of 120 to 160 degrees. The s-shaped curve can have a first curve and a second curve, the second curve distal to the first curve, and the pre-shaped curve can be aligned in substantially the same direction as the second curve. The pointed distal end can include an anchor. The curved middle portion can be preset to mimic a set bend in an occlusion-crossing catheter.

In general, in one embodiment, a method of re-entering a true lumen during occlusion-crossing includes orienting a distal end of a catheter having a bend therein towards the true lumen of a vessel; introducing a stylet through a guidewire channel of the catheter until a curved middle portion of the stylet aligns with the bend in the catheter and a pointed distal end of the stylet extends out of a distal end of the catheter; advancing the stylet such that the pointed distal end pierces through a wall of the vessel; and directing the catheter over the stylet and into the true lumen of the vessel.

This and other embodiments can include one or more of the following features. The method can further include orienting the stylet within the catheter such that the pointed distal end of the stylet curves sharply towards the vessel wall before advancing the stylet. The method can further include reorienting the catheter within the true lumen after directing the catheter of the stylet. Reorienting the catheter can include reorienting without puncturing an opposite vessel wall. The method can further include determining an orientation of the stylet based upon an alignment of the curved middle portion with the bend in the catheter. The catheter can further include a proximal portion, the proximal portion and the curved middle portions can have substantially circular cross-sections, and the pointed distal end can have a flatted portion and can have a substantially oblong cross-section. The method can further include using image guidance to orient the catheter.

In general, in one embodiment, an assembly for re-entry into a vessel includes a catheter and a stylet. The catheter includes a pre-set curve. The stylet includes an elongate body having a proximal portion, a middle flexible portion, and a distal stiff portion. When the stylet is inserted into the catheter, the flexible portion is configured to conform to the pre-set curve and the distal stiff portion is configured to at least partially straighten the pre-set curve. The flexible portion has a length such that the flexible portion can align with the pre-set curve both while the distal stiff portion remains inside the catheter and while the distal stiff portion extends distally from a distal end of the catheter.

This and other embodiments can include one or more of the following features. The distal stiff portion can include a sharp pointed end. The middle flexible portion can include a flexible coil. The proximal portion can be stiffer than the middle flexible portion.

In general, in one embodiment, an assembly for re-entry stylet for re-entry into a vessel includes a catheter and a stylet. The catheter includes a pre-set curve. The stylet includes a flexible elongate body having a pointed distal end. The stylet further includes a stiff tube concentric with the flexible elongate body, the flexible elongate body axially movable relative to the stiff tube. When the stylet is inserted into the catheter, the flexible portion is configured to conform to the pre-set curve, and the flexible elongate body is configured to at least partially straighten the pre-set curve.

This and other embodiments can include one or more of the following features. The flexible elongate body can include a pre-set curve configured to match the pre-set curve of the catheter. The flexible elongate body can include a shape memory material.

In general, in one embodiment, a stylet for re-entry into a vessel includes an elongate body having a pointed distal tip. The stylet includes a coiled member attached to the pointed distal tip. The coiled member includes a relaxed configuration where the coiled member extends over the pointed distal portion and a compressed configuration wherein the coiled member is compressed to expose at least a portion of the pointed distal tip.

Methods of using the stylets to reenter a lumen, such as for occlusion crossing, are also described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is a side view of the distal end of an exemplary directional re-entry stylet.

FIG. 1B is a close-up of the distal tip of the directional re-entry stylet of FIG. 1B.

FIG. 2A is a schematic of a directional re-entry stylet such as the one shown in FIG. 1A.

FIG. 2B is a close-up of the distal tip shown in FIG. 2A.

FIG. 2C is a close-up of the junction shown in FIG. 2A.

FIG. 3A is a schematic of an exemplary aligning re-entry stylet having a central flexible section.

FIG. 3B is a close-up of the flexible section of the aligning re-entry stylet of FIG. 3A.

FIG. 4A shows the re-entry stylet is aligned within the device such that the angle of the pre-set curve is not changed by the stylet. FIG. 4B shows the exemplary CTO crossing device straightened using the re-entry stylet. FIG. 4C shows the exemplary CTO crossing device with the re-entry stylet extending from the distal end.

FIG. 7A shows the stylet placed such that both the outer tube and the inner elongate body are proximal of the pre-set curve. FIG. 7B shows the outer tube moved distal to the pre-set curve such that the pre-set curve is straightened. FIG. 7C shows the outer tube positioned proximal to the pre-set curve and the inner elongate body extended out the distal end of the catheter. FIG. 7D shows the outer tube moved distal to the pre-set curve such that the pre-set curve is straightened and the inner elongate body extended out the distal end of the catheter.

FIG. 10A shows a spring-loaded stylet in passive mode. FIG. 10B shows a spring-loaded stylet in active mode.

FIG. 12A shows the stylet pointing out of the catheter. FIG. 12B shows the stylet piercing through the vessel wall. FIG. 12C shows the catheter reentering the true lumen over the stylet. FIG. 12D shows the catheter reoriented within the true lumen.

FIG. 13A shows the stylet piercing the vessel wall. FIG. 13B shows the catheter reentering the true lumen over the stylet. FIG. 13C shows the catheter reoriented within the true lumen.

FIG. 14A shows the stylet within the catheter. FIG. 14B shows the stylet piercing the wall. FIG. 14C shows the catheter reentering the true lumen over the stylet. FIG. 14D shows the stylet straightening the catheter to reorient it within the true lumen.

DETAILED DESCRIPTION

Figure 11A:
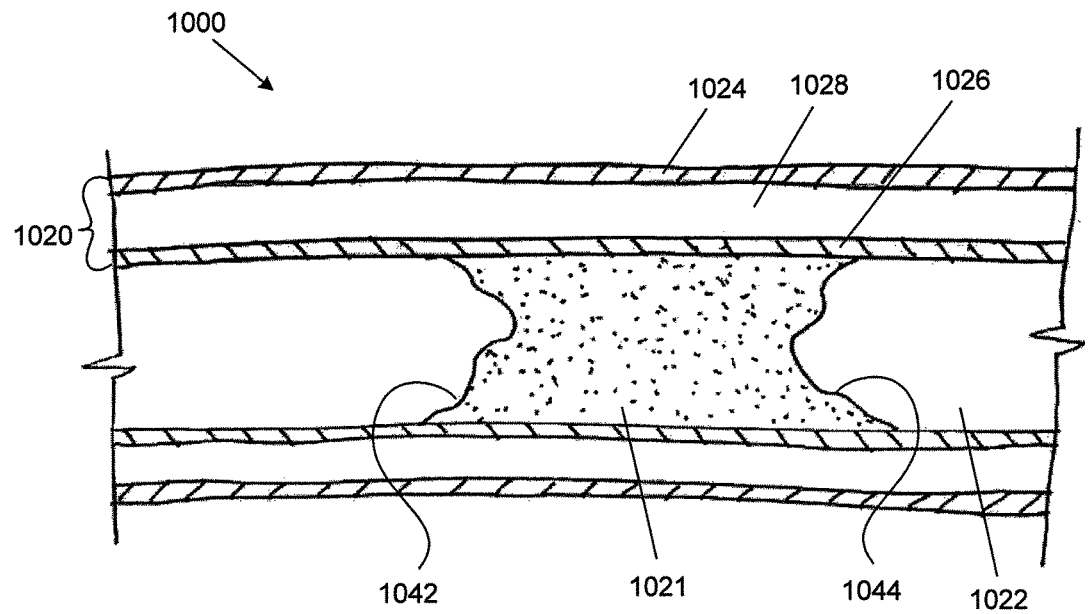
FIG. 11A shows an exemplary occluded vessel.
Figure 11B:
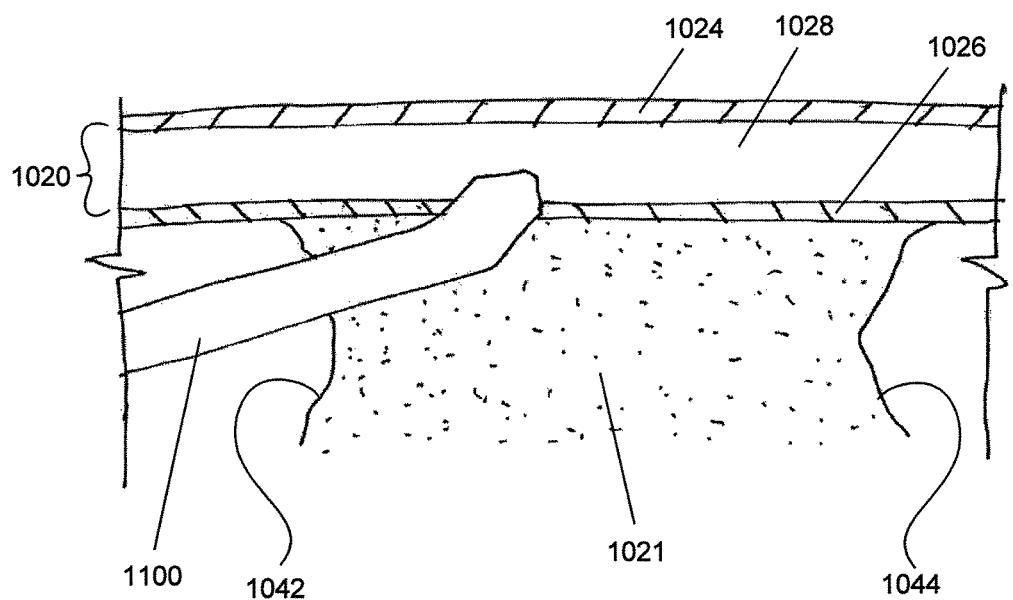
FIG. 11B shows an occlusion-crossing catheter that has extended into the subintimal layers of the occluded vessel of FIG. 11A.
Figure 11C:
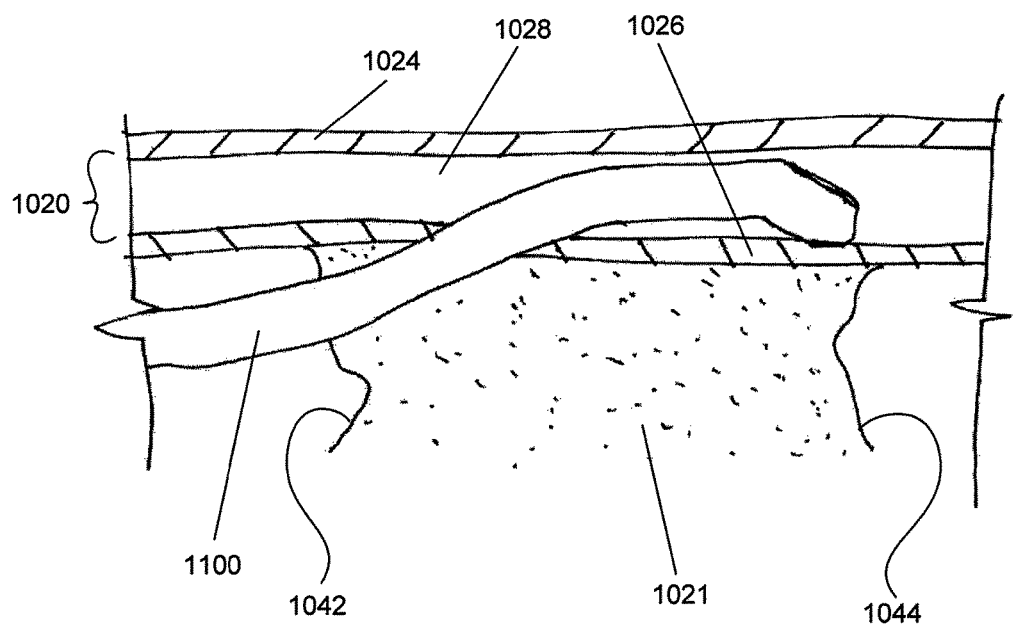
FIG. 11C shows the occlusion crossing catheter of FIG. 11B trapped in the subintimal layer.

Referring to FIG. 11A, an occluded vessel 1000 includes a lumen 1022 (or "true lumen") with an occlusion 1021 and an arterial wall 1020. The arterial wall 1020 can include an innermost intimal layer 1026, which can include the endothelium, the subendothelial layer, and the internal elastic lamina. A relatively soft medial layer 1028 (also called the "subintimal space") surrounds the intimal layer 1026, which is then surrounded by an advential layer 1024. The proximal and distal caps 1042, 1044 of the occlusion are generally very hard relative to the rest of the occlusion. As a result, when a guidewire or occlusion-crossing device hits one of the caps 1042, 1044, it can often end up deflecting off of the cap 1042, 1044 and extending through the intimal layer 1026 and into the relatively soft medial layer 1028. For example, referring to FIG. 11B, an occlusion-crossing device 1100 has extended into the subintimal space within the medial layer 1028, which can define a "false lumen." As shown in FIG. 11C, the occlusion-crossing device 1100 can then get trapped in the subintimal space outside the true lumen 1022.

Stylets are described herein that can be used to assist in occlusion-crossing within a blocked vessel. For example, in some embodiments, the stylets described herein can redirect occlusion-crossing devices back into the true lumen of a vessel. In addition or alternatively, the stylets described herein can straighten and/or deflect an occlusion-crossing device to orient the device as needed.

In general, any of the stylets described herein can have a deflection region at the distal end thereof to provide directionality and steerability of the catheter. The deflection region can, for example, be imparted by a pre-shaped curve that matches an inner lumen of a catheter. The deflection region can also be imparted by an s-shaped curve at the distal tip of the stylet that helps orient and direct the stylet back into the true lumen of a vessel. In some embodiments, the deflection region can have a flattened profile to provide stability during piercing of the vessel wall into the true lumen.

Any of the stylets described herein can further be designed to include both flexible and stiff portions along the longitudinal axis to aid both in conforming the stylet to a catheter in which it is inserted and in providing the necessary stiffness to puncture a vessel wall. The stylets can include a proximal portion, a middle flexible portion, and a distal stiff portion. The middle flexible portion can be flexible enough to conform to a curve of a catheter in which the stylet is inserted while the distal stiff section can be stiff enough to provide a piercing force to guide the stylet into a true lumen of a vessel.

The stylets described herein can include an inner flexible body and an outer stiff tube. The flexible body and outer stiff tube can be moved axially relative to one another to provide the desired stiffness or flexibility for the stylet, e.g., to provide flexibility to extend around a pre-set curve in a catheter or to provide stiffness to straighten the pre-set curve. In other embodiments, the inner body can be stiff while the outer tube can be flexible.

Furthermore, the stylets described herein can include a coiled member attached to the distal tip to provide protection for the tip when in the extended configuration and allow for exposure of the tip when compressed.

Referring to FIGS. 1A through 2C, an exemplary directional re-entry stylet 100 includes a proximal portion 101, a middle curved portion 102, and a distal pointed end 103.

The proximal portion 101 can be a wire, such as a stainless steel wire. The wire can be chosen to have a stiffness that corresponds to the required amount of pushability and column support needed for the particular wire diameter used. The proximal portion 101 can further have a substantially round cross-section. The proximal portion 101 can be approximately 0.010 to 0.035 inches in diameter, such as approximately 0.015 inches in diameter.

The curved middle portion 102 can have a pre-set curve 105 that is flexible enough to follow the contours of lumen of a catheter but stiff enough to orient its curved shape to align with a bent section of an the catheter. For example, referring to FIG. 2B, the pre-set curve 105 can form an angle α of between 120 degrees and 180 degrees, such as between about 130 degrees and 170 degrees, for example approximately 150 degrees. The pre-set curve can advantageously ensure that the stylet 100 aligns properly with the catheter in which it is inserted, thereby allowing the catheter to maintain its curved form and ensuring proper steering of the catheter.

Further, in other embodiments, the pre-set curve 105 can be stiff enough to change the deflection region of the catheter in which it is inserted. Thus, for example, the pre-set curve 105 could force the catheter into a set angle of between 120 degrees and 180 degrees, such as between about 130 degrees and 170 degrees, such as 150 degrees. In some embodiments, rather than having a pre-set curve, the curved middle portion 102 can have a flexible portion, such as a necked section or a coiled section, to allow the middle portion 102 to flexibly conform to the shape of a catheter in which it is inserted.

The curved middle portion 102 can be formed of a wire, such as a nitinol wire. The curved middle portion can further have a substantially round cross-section. The curved middle portion 102 can have a diameter of approximately 0.008 inches to 0.015 inches, such as approximately 0.012 inches in diameter. In some embodiments, the middle portion 102 is formed separately from the proximal portion 101 and connected through a junction 106, such as a hypotube joint (see FIG. 2C) or a laser welded sleeve. In other embodiments, the middle portion 102 and proximal portion 101 can be formed of a single piece of material, such as a single wire.

The pointed distal end 103 can include an s-shaped curve 107 (see FIGS. 1B and 2B), i.e., include two opposing curves 109 and 111 along the longitudinal axis. Referring to FIG. 2B, the proximal-most curve 109 of the s-shaped curve 107 can have an angle β of between approximately 90° to 180°, such as between about 120° to 160°, such as 150°, while the distal-most curve 111 of the s-shaped curved 107 can have an angle θ of between approximately 90° to 180°, such as 120° to 160°, such as 150°. The s-curve 107 can be oriented such that the distal end 103 points in approximately the same direction as the end of the catheter, as set by the pre-set curve 105. That is, referring to FIG. 2B, the angle α can be oriented in approximately the same direction as the angle θ while the angle β can be aligned in substantially the opposite direction. Angles β and θ can be approximately equal to one another. Further, having the distal end 103 point in the same direction as the distal end of the catheter (set by the jog in the catheter) advantageously provides more of an angle for re-entry into a true lumen. Finally, the alignment of the angle α with the angle θ also advantageously provides an indication as to the orientation of the stylet.

The distal tip 115 (between the distal-most point and the distal curve 111) can be less than about 3 mm, such as between about 1-2 mm. Further, the stylet 100 itself can be about 150 cm-300 cm in length, such as 175 cm to 200 cm, such as approximately 180 cm in length. Thus, the distal tip 115 can comprises less than 1%, such as less than 0.5% of the total length of the stylet 100. The short length of the distal tip 115 relative to the length of the entire stylet 100 advantageously provides that the stylet will advance only partially through the vessel wall and back into the true lumen during reentry (i.e., to avoid puncturing the opposite wall of the vessel).

In other embodiments, rather than having an s-shaped curve 107, the pointed distal end 103 can include a J-shaped curve, i.e. a hook, that can be used to force the stylet 100 (and thus the catheter in which it is inserted) back towards a true lumen.

The pointed distal end 103 can further included a flattened portion, i.e., a portion in which the otherwise round cross-section has been flattened to include two substantially parallel and flat surfaces, e.g., such that a cross-section of the flattened portion is substantially oblong. As shown in FIG. 1B, the s-curve 107 can be located within the flattened portion such that the shape of the "s" is formed on the flattened surface. This flattened portion can advantageously help to hold the pre-set curve as it is forced against tissue. The flattened portion can also advantageously provide rigidity as the tip of the stylet is forced into tissue.

Further, the pointed distal end 103 can be tapered from the proximal end to the distal end. For example, the distal end can be 0.012 inches in diameter and can taper down to a tip 115 of approximately 0.005 inches in diameter. The tip 115 of the pointed distal end 103 can be sharp, i.e., can be configured to penetrate tissue, such as subintimal layers of a blood vessel. The taper can advantageously provide smooth dilation or entry into a vessel wall or occlusion.

Figure 12A:
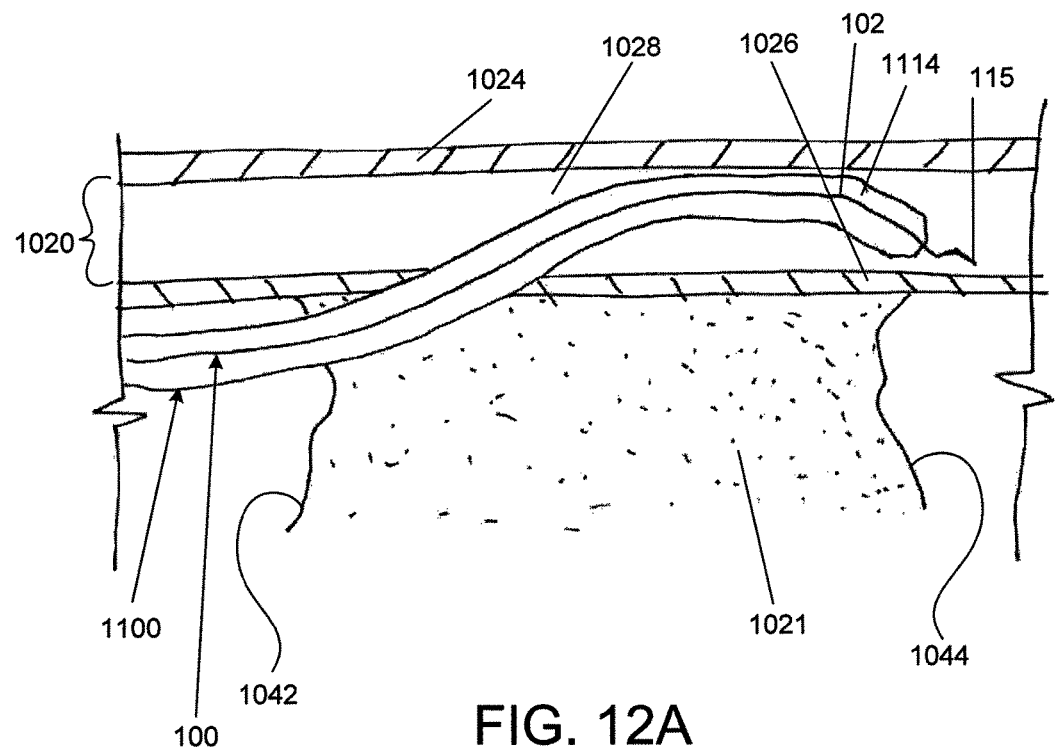
FIGS. 12A-12D show use of a stylet similar to the stylet of FIG. 1A to guide a catheter from the subintimal layer back into the true lumen.
Figure 12B:
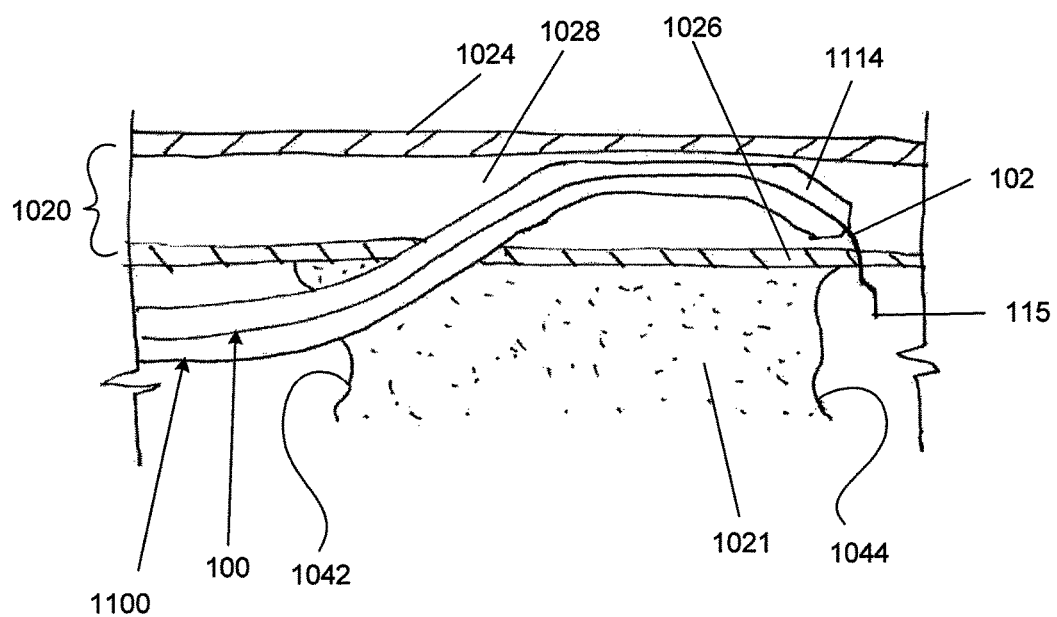
Figure 12C:
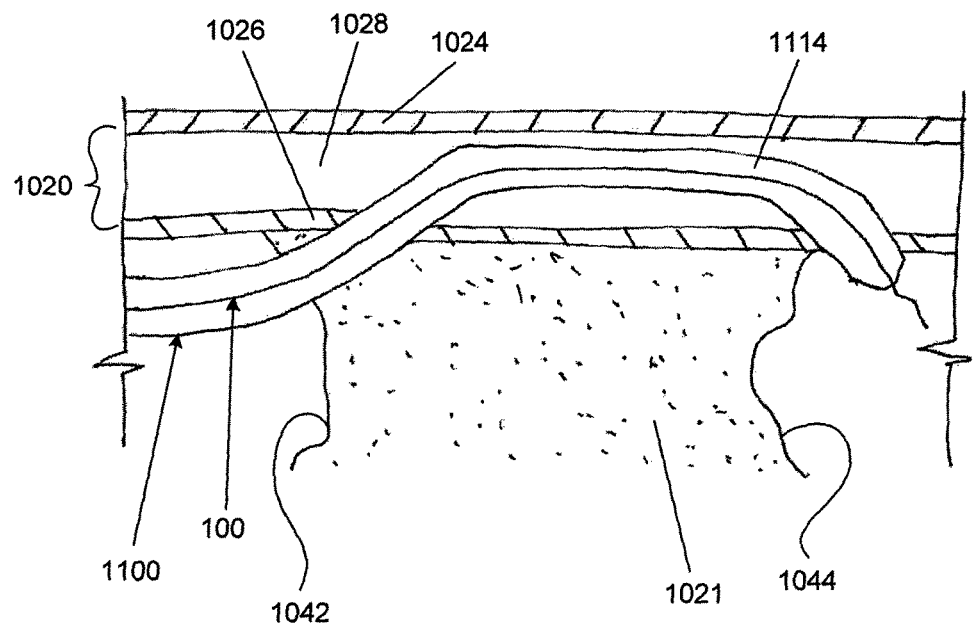
Figure 12D:
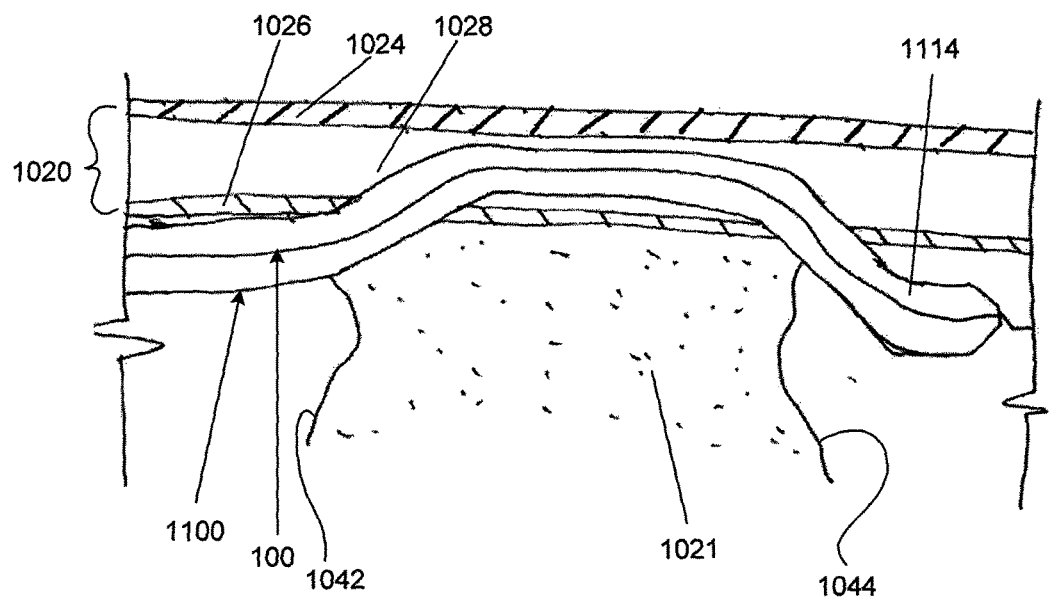

Referring to FIGS. 12A-12D, in one embodiment, a stylet 100 can be used as a re-entry tool for an occlusion-crossing catheter 1100 that has exited the true lumen 1022 and entered the subintimal layer (e.g., medial layer 1028). The stylet 100 can be placed through a guidewire channel of a catheter 1100. The catheter 1100 can have a fixed bend 1114, which can be rotated to point towards the true lumen 1022. As shown in FIG. 12A, the stylet 100 can be threaded through the catheter 1100 such that the curved middle portion 102 aligns with the bend 1114 in the catheter 1100 and such that the tip 115 points out the distal end of the catheter. Because the angle of the curved middle portion 102 is pointed in the same direction as the distal-most curve of the s-shaped curve, and because the fixed bend 1114 has been oriented towards the true lumen 1022, the distal tip 115 will also point towards the true lumen 1022. Further, referring to FIG. 12B, because the curved middle portion 102 has a pre-set curve, the curve will hold the stylet's orientation as it is advanced. Thus, as the stylet is advanced, the distal tip 115 will curve even more sharply towards the true lumen 1022 and pierce back through the tissue of the vessel wall 1020 at a steep angle (e.g. at an angle of between approximately 60 and 90 degrees relative to the wall). Referring to FIG. 12C, the catheter 1100 can then be advanced over the stylet 100 back into the true lumen 1022. As shown in FIG. 12D, to reorient the catheter 1100 towards down the axis of the lumen 1022, the catheter can be rotated approximately 180 degrees to point the fixed bend 1114 down the lumen 1022. In some embodiments, this process can be used to pass entirely by an occlusion (as shown in FIGS. 12A-12D). In other embodiments, the stylet 100 can direct the catheter 1100 back into the occlusion at a point between the proximal 1042 and distal 1044 caps of the occlusion 1021, and then the catheter 1100 can be used to finish crossing through the lesion, such as will a rotating drill feature on the distal end of the catheter.

Referring to FIGS. 3A-3B, an aligning re-entry stylet 200 includes a proximal portion 201, a middle flexible portion 202, and a distal stiff portion 203.

The proximal portion 201 can be a wire, such as a stainless steel wire. The wire can be stiff enough to provide pushability through a catheter. The proximal portion 201 can be approximately 0.010 to 0.038 inches in diameter, such as approximately 0.015 inches in diameter.

The middle flexible portion 202 is configured to be flexible so as to conform to the shape of a catheter in which it is inserted. In one embodiment, the flexible portion 202 is a coil, such as a coil of wire. The coil can have an outer diameter of 0.010 to 0.038 inches, such as approximately 0.014 inches and an inner diameter of 0.005 to 0.010 inches, such as approximately 0.008 inches. The coil can be made, for example, of stainless steel. The wire forming the coil can have a diameter of 0.001 to 0.005 inches, such as approximately 0.003 inches. In another embodiment, the middle flexible portion 202 could be a necked portion in a wire. In another embodiment, the middle flexible portion 202 can be a separate flexible material, such as a plastic. In another embodiment, the middle flexible portion 202 can be a hypotube that has been cut, such as laser cut, into a flexible spiral or plurality of rings along a spine.

The proximal stiff portion 203 can be stiff enough to straighten a prebent catheter in which it is inserted. For example, the proximal stiff portion can be made of a stainless steel wire. The wire can have a diameter, for example, of 0.010 to 0.038 inches, such as approximately 0.015 inches. The distal portion 203 can further include a sharp tip 212, such as a needle-like or pointed end. In some embodiments, the sharp tip 212 can be angled to assist in re-entry.

Figure 4A:
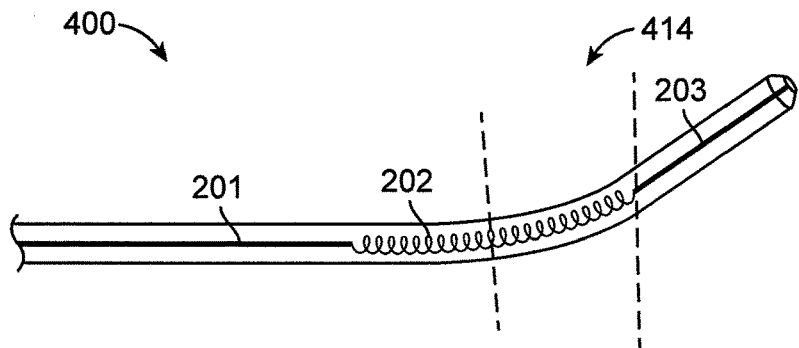
FIGS. 4A-4C show the re-entry stylet of FIG. 3A in an exemplary CTO crossing device with a pre-set curve.
Figure 4B:
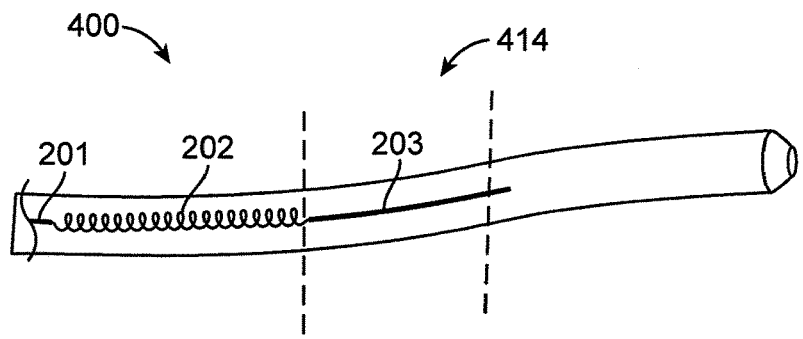
Figure 4C:
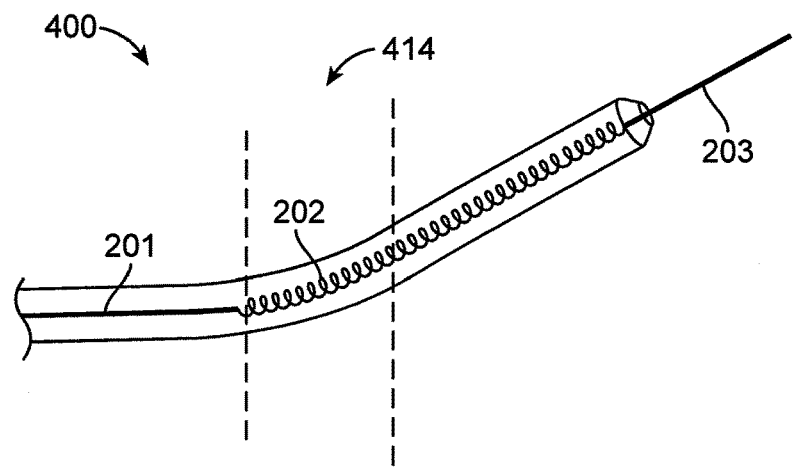

The flexible portion 202 can have a length such that the flexible portion can align with a pre-set curve 414 in a catheter 400 in which it is inserted both while the distal stiff portion 203 remains inside the catheter 400 (FIG. 4A) and while the distal stiff portion 203 extends distally from the distal end of the catheter 400 (FIG. 4C).

In use, referring to FIGS. 4A-4C, the stylet 200 can be inserted into a catheter, such as a catheter 400 having a pre-bent curve 414. As shown in FIG. 4A, the stylet 200 can be inserted such that the flexible portion 202 aligns with the pre-bent curve 414 while the distal portion 203 remains inside the catheter. This alignment can advantageously provide little interference with the catheter as the catheter is used under normal conditions.

The stylet 200 can also be inserted such that the distal stiff portion 203 aligns with the pre-bent curve 414, thereby straightening the curve, as shown in FIG. 4B. This alignment can advantageously make directly entry into an occlusion easier, i.e., placing force on a straightened catheter, from within the true lumen, can provide a straight trajectory into the occlusion.

Figure 13A:
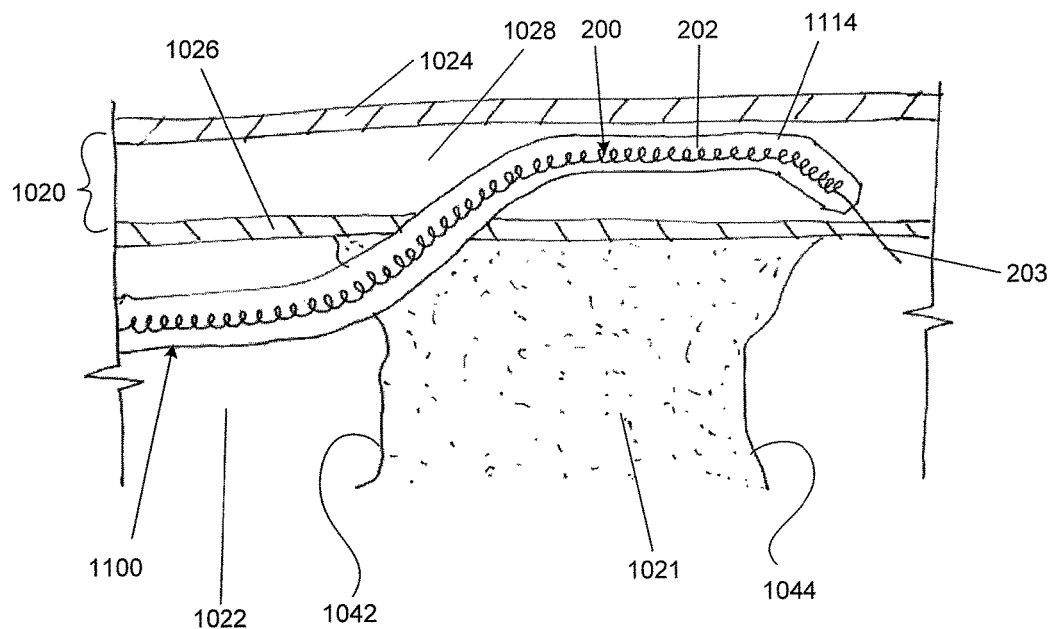
FIGS. 13A-13C show use of a stylet similar to the stylet of FIG. 4A to guide a catheter from the subintimal layer back into the true lumen.
Figure 13B:
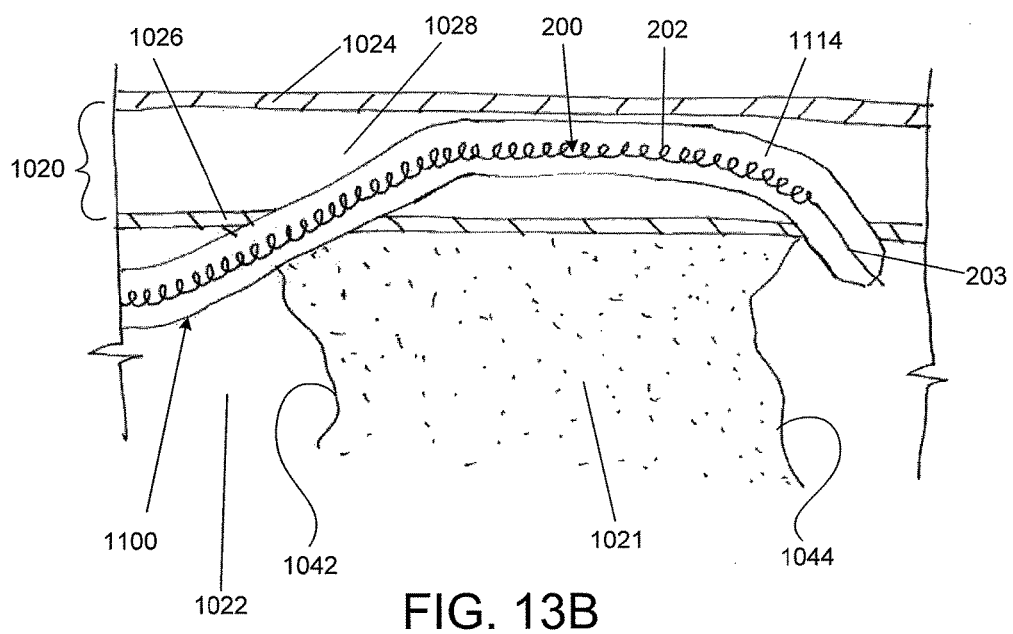
Figure 13C:
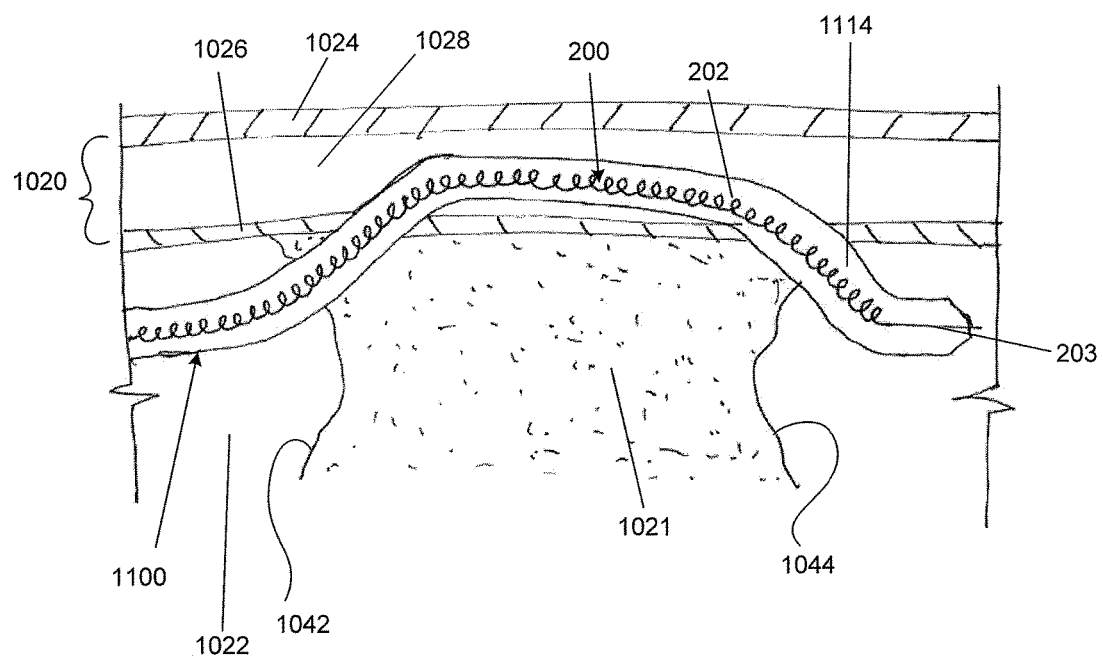

Finally, as shown in FIG. 4C, the stylet 200 can be inserted such that the flexible portion 202 aligns with the pre-bent curve 414 while the distal portion 203 extends out of the distal end of the catheter 400. This alignment can advantageously assist in re-entry from a false lumen to a true lumen, i.e., the curve of the catheter 400 can be turned towards the true lumen, and the distal end 203 of the stylet 200 can be used to pierce the vessel and guide the catheter 400 back into the true lumen. For example, FIGS. 13A-13C show a stylet 200 used as a re-entry tool for an occlusion-crossing catheter 1100 that has exited the true lumen 1022 and entered the subintimal layer (e.g., medial layer 1028). The stylet 200 can be placed through a guidewire channel of the catheter 1100. The catheter 1100 can have a fixed bend 1114, which can be rotated to point towards the true lumen 1022. As shown in FIG. 13A, the stylet 200 can be threaded through the catheter 1100 such that the flexible portion 202 aligns with the fixed bend 1114 while the distal portion extends out of the distal end of the catheter 1100. Because the fixed bend 1114 has been oriented towards true lumen 1022, the sharp distal portion 203 will also point towards the true lumen 1022, making it easy to pierce the wall 1020. Referring to FIG. 13B, the catheter 1100 can then be advanced over the stylet 200 back into the true lumen 1022. As shown in FIG. 12C, to reorient the catheter 1100 towards down the axis of the lumen 1022, the catheter can be rotated approximately 180 degrees to point the fixed bend 1114 down the lumen 1022. In some embodiments, this process can be used to pass entirely by an occlusion (as shown in FIGS. 13A-13C). In other embodiments, the stylet 200 can direct the catheter 1100 back into the occlusion at a point between the proximal 1042 and distal 1044 caps, and then the catheter 1100 can be used to finish crossing through the lesion, such as with drilling features on the catheter 1100.

Figure 5A:
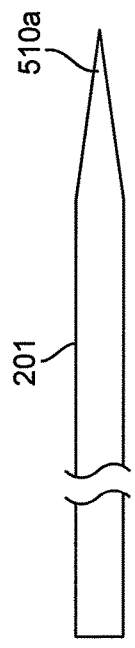
FIGS. 5A-5C show an exemplary process for producing the stylet of FIG. 3A.
Figure 5B:
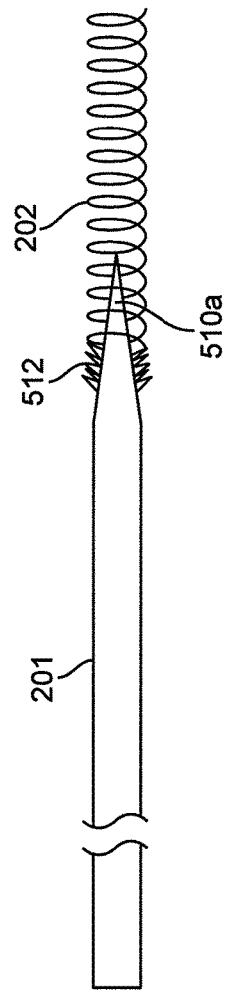
Figure 5C:
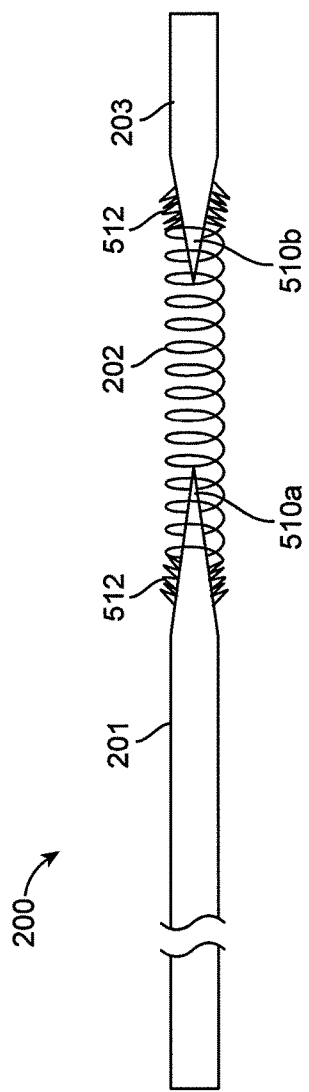

Referring to FIGS. 5A-5C, a stylet 200 can be made, for example, by grinding two mandrels to a taper 510a,b (the mandrels will form the proximal and distal ends, respectively), and then placing the tapers 510a,b inside a coil 202 and connecting the coil 202 to each taper 510a,b, as shown in FIG. 5C.

Figure 6:
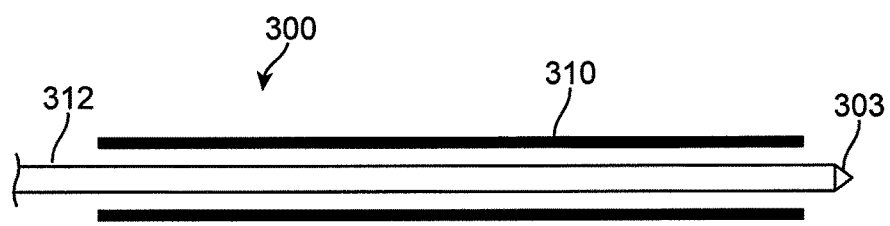
FIG. 6 shows an exemplary bilayer re-entry stylet having a stiff outer tube and a flexible inner elongate body.

Referring to FIG. 6, a stylet 300 can include an outer tube 310 and an inner elongate body 312 axially movable relative to the outer tube 310. The outer tube 310 can be stiff relative to the inner elongate body 312. The inner elongate body 312 can have a pointed or sharp distal end 303 similar to the distal end of the stylets 100, 200. The inner elongate body 312 and/or the outer tube 310 can be made of a metal, such as stainless steel or nitinol.

Figure 7A:
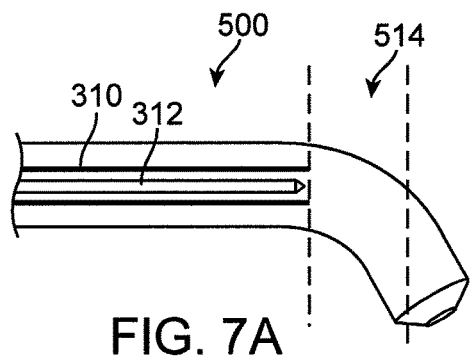
FIGS. 7A-7D shows the bilayer re-entry stylet of FIG. 6 in an exemplary CTO crossing device with a pre-set curve.
Figure 7B:
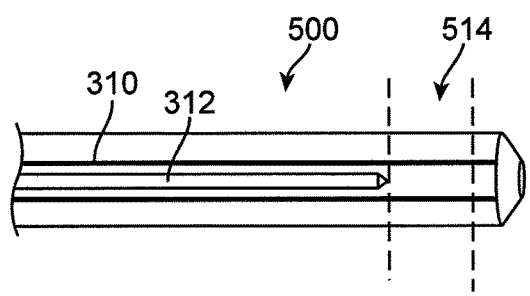

Further, referring to FIGS. 7A-7B, the stylet 300 can be configured to be placed within a lumen of a catheter, such as a catheter 500 having a pre-set curve 514. The outer tube 310 can be stiff relative to the pre-set curve 514 while the inner elongate body 312 can be flexible relative to the pre-set curve 514. As a result, the outer tube 310 can be used to straighten the pre-set curve 514 while the inner elongate body 312 can conform to the pre-set curve 514.

Figure 7C:
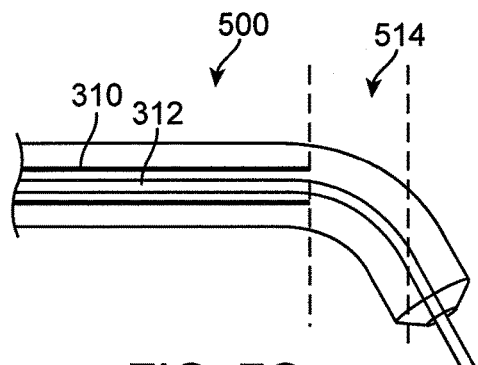
Figure 7D:
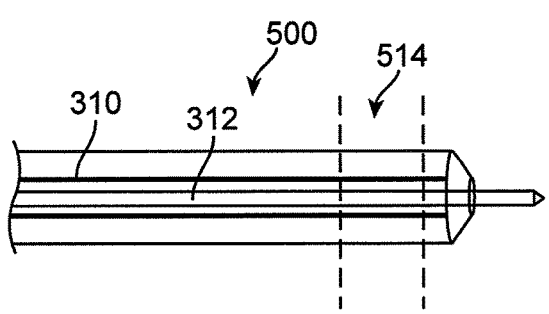

Thus, referring to FIG. 7A, the stylet 300 can be placed such that the entire stylet 300 is proximal to the pre-set curve 514. As shown in FIG. 7B, if the outer tube 310 is advanced distal to the pre-set curve 514, then the pre-set curve 514 of the catheter 500 will substantially straighten out. Such straightening can be advantageous, for example, if the catheter 500 is being used to cross a CTO from within the true lumen, as force can be applied on the CTO from substantially perpendicular to the CTO. Referring to FIG. 7D, the inner elongate body 312 can also be extended out of the distal end of the catheter while the catheter is in a straightened position to assist with crossing the CTO (e.g. such that the pointed distal end 303 can cut through the occlusion or pierce the proximal or distal cap). On the other hand, as shown in FIG. 7C, if only the inner elongate body 312 is advanced distal to the pre-set curve 514, then the pre-set curve 514 can maintain its shape while the pointed distal end 303 can be advanced out of the catheter 500. This configuration can be advantageous, for example, for re-entry form a false lumen to a true lumen, i.e. the curve 514 of the catheter 514 can be turned towards the true lumen, and the pointed distal end 303 of the inner elongate body 312 can be used to pierce the vessel and guide the catheter 500 back into the true lumen.

Figure 14A:
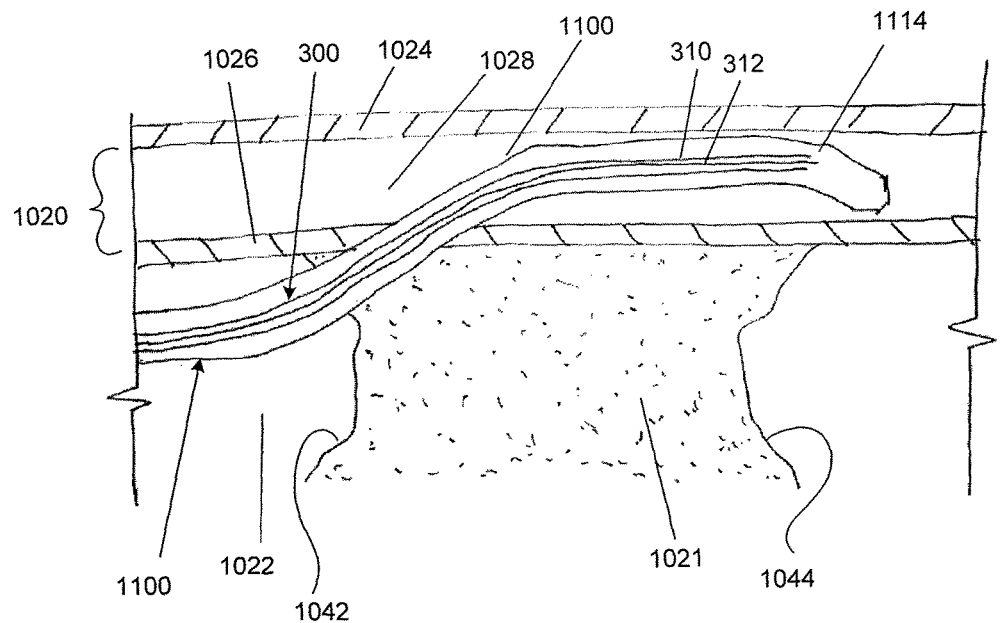
FIGS. 14A-14D shows use of a stylet similar to the stylet of FIG. 6 to guide a catheter from the subintimal layer back into the true lumen.
Figure 14B:
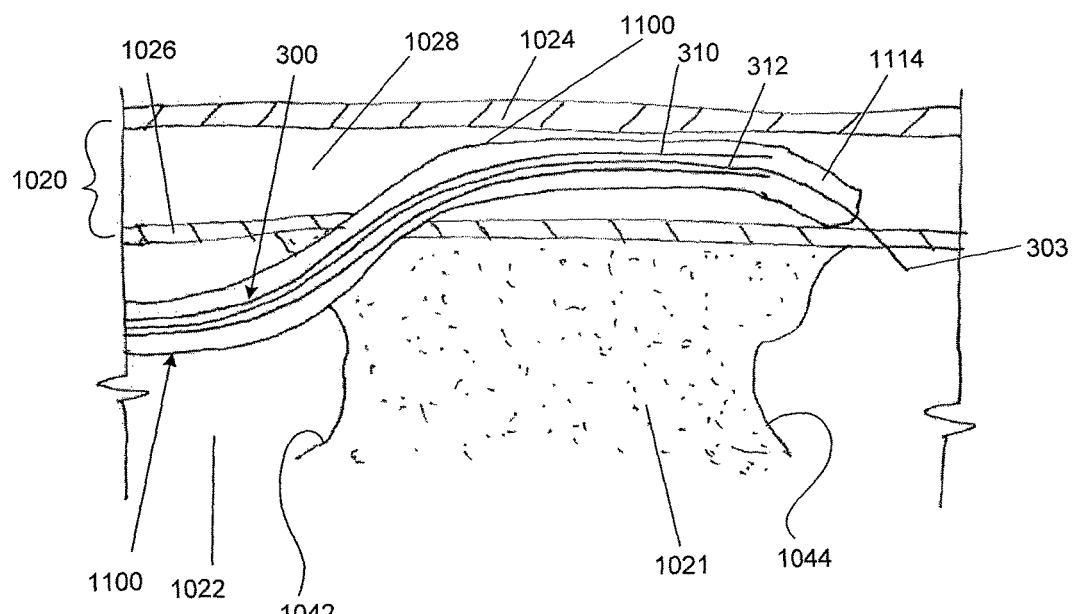
Figure 14C:
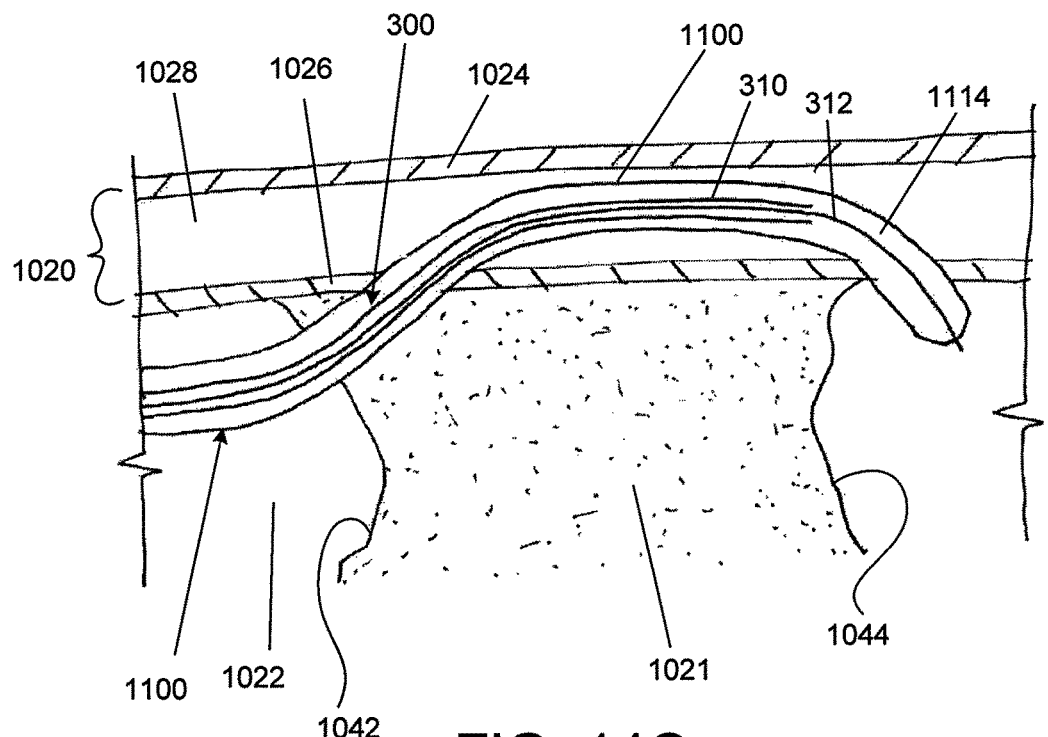
Figure 14D:
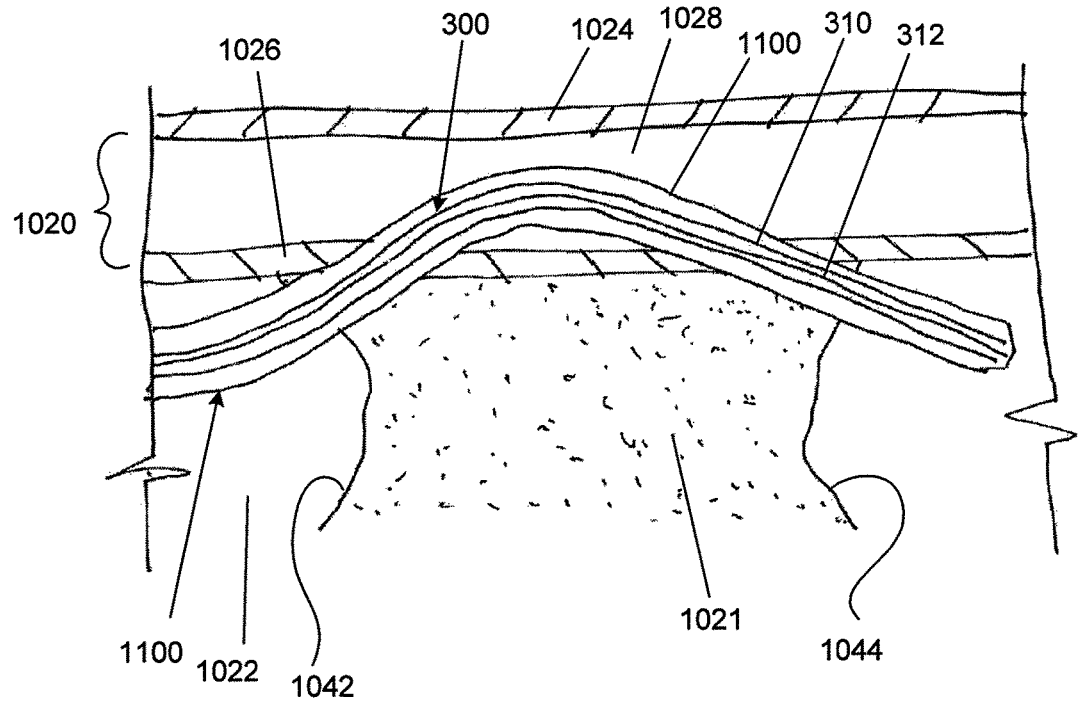

FIGS. 14A-14D show a stylet 300 used as a re-entry tool for an occlusion-crossing catheter 1100 that has exited the true lumen 1022 and entered the subintimal layer (e.g., medial layer 1028). As shown in FIG. 14A, the stylet 300 can be placed through a guidewire channel of the catheter 1100. The catheter 1100 can have a fixed bend 1114, which can be rotated to point towards the true lumen 1022. Referring to FIG. 14B, the inner elongate body 312 can then be extended towards the true lumen 1022. Because the fixed bend 1114 has been oriented towards the true lumen 1022, the pointed distal end 303 will also point towards the true lumen 1022, thereby allowing it to pierce the vessel wall 1020 as it is extended. Referring to FIG. 14C, the catheter 1100 can then be advanced over the stylet 300 back into the true lumen 1022. As shown in FIG. 12D, the outer tube 310 can then be extended within the catheter 1100 such that it straightens the fixed bend 1114. Such straightening of the fixed bend 1114 will point the catheter 1100 more directly down the true lumen 1022. In some embodiments, this process can be used to pass entirely by an occlusion (as shown in FIGS. 14A-14D). In other embodiments, the stylet 300 can direct the catheter 1100 back into the occlusion at a point between the proximal 1012 and distal 1044 caps, and then the catheter 1100 can be used to finish crossing through the lesion.

In some embodiments, the inner elongate body 312 can have a pre-set curve that substantially matches the pre-set curve 514 of the catheter 500. For example, the inner elongate body 312 can be made of a shape memory material, such as nitinol, to set the curve. Having this matched curve can advantageously help with re-entry into the true lumen. That is, if the user steers the directionality of the catheter 500 towards the true lumen, then when the curved inner elongate body 312 exits, it will curve and be directed towards the true lumen even more than the catheter itself, helping to avoid deflection off of the vessel wall.

In general, a sharp distal tip of any of the stylets described herein may be protected or covered until deployment into tissue. For example, a spring loaded sheath or housing can be pushed distally along the long axis of the tip to expose the sharp tip. For example, as shown in FIGS. 10A and 10B, a stylet 900 can include a spring-loaded mechanism 902 on the distal end of a stylet body 910. Thus, a coiled member 904 can be configured to extend over the tip 906 of the stylet, which can be sharp and/or tapered. Referring to FIG. 10A, in the passive mode, i.e. before contacting tissue, the coiled member 904 can cover the tapered or sharp end of the stylet so that the end is atraumatic in non-targeted areas. Once the location of re-entry is reached, the tip 906 can be advanced into the tissue, thus activating the spring mechanism (shown in FIG. 10B) as the coil compresses and exposes the penetrating tip 906.

The length of exposed tip 906 can be controlled by placing the coiled member 904 in the desired location along the stylet body 910. Accordingly, the initial length of the tip 906 that is exposed through the vessel wall or occlusion can be limited by the coiled member 904, advantageously avoiding over-puncturing and possibly hitting the opposing vessel wall. Further, the pitch of the coiled member 904 can be chosen based upon the desired spring force required to penetrate or puncture the tissue, such as based upon the type or thickness of the tissue. Once the tip has been pushed fully through, the coiled member 904 can act as a temporary stop, providing tactile feedback for the user and allowing the user to adjust the angle or orientation of the stylet tip. Additional force can then be placed on the stylet 900 to push the coiled member 904 through. Once the proximal end of the coiled member 904 is fully advanced through the tissue, the coiled member can relax, allowing the stylet 900 to be in passive mode again as it traverses through the vessel.

Although a coiled member 904 is shown in FIGS. 10A and 10B, other spring loaded mechanisms 902 are possible. Advantageously, spring loaded mechanisms 902 on the stylet can help control depth of penetration and also provide a safer method of controlling re-entry. The spring-loaded mechanism 902 can be used with a traditional stylet or with any of the stylets described herein.

Figure 8:
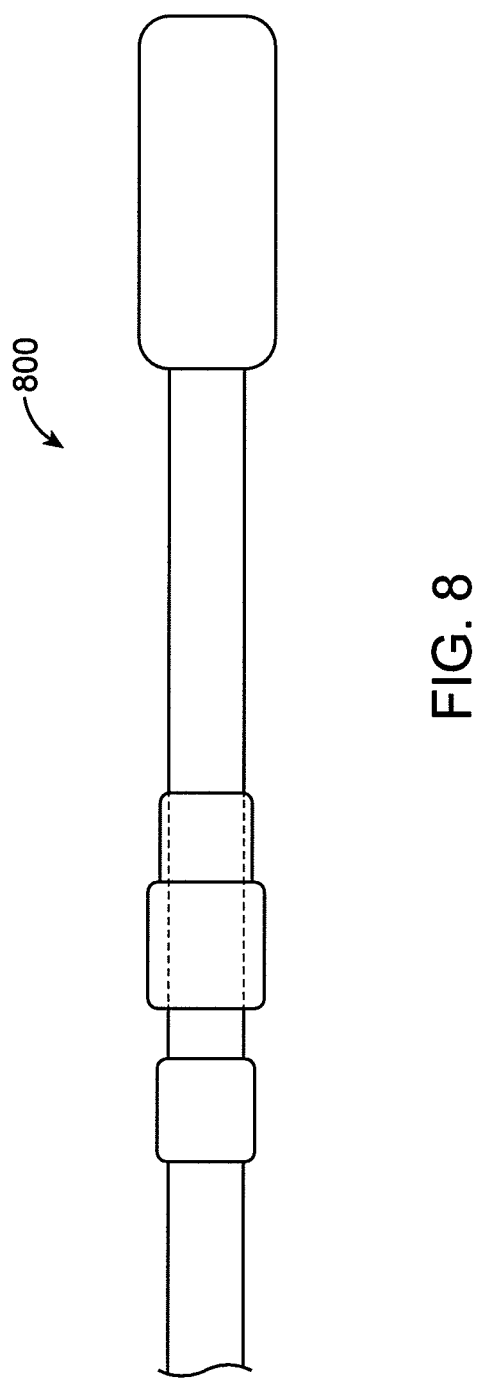
FIG. 8 shows an exemplary manipulator for steering a re-entry stylet.

Referring to FIG. 8, a handle 800 can be used to steer any of the stylets described herein. The handle 800 can include a locking mechanism to lock it onto the proximal end of the device, such as a luer fitting. In one embodiment, the handle 800 can have predefined positions that align the stylet appropriately with the catheter. For example, if the handle 800 is used with the stylet 200, the handle can lock the stylet 200 in a first position where the stylet 300 is proximal of the bend in the catheter, thereby allowing the main body of the catheter to have extra support. The handle can also lock the stylet 200 in a second position where the distal stiff section of the stylet 200 is in the prebent section of the catheter, thereby straightening the catheter. Finally, the handle 800 can lock the stylet 200 in a third position where the distal part of the stylet 200 sticks out of the distal tip of the catheter, thereby enabling re-entry into the true lumen. The handle 800 can include similar predefined positions when used with the other stylets described in here.

Figure 9A:
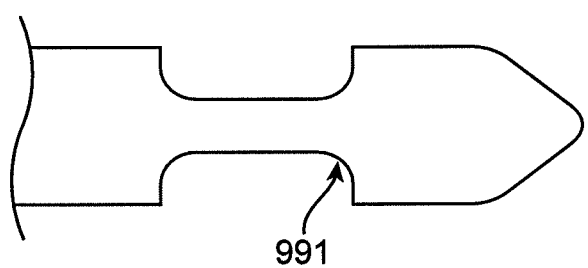
FIG. 9A shows an exemplary stylet tip having a hook anchoring mechanism.
Figure 9B:
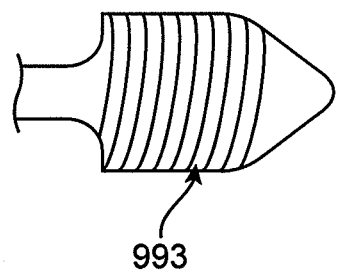
FIG. 9B shows an exemplary stylet tip having a drill anchoring mechanism.

Any of the embodiments of stylets herein can include an anchoring mechanism on or near the distal tip. For example, the distal end can include a hook 991 as shown in FIG. 9A or a drill tip 993 as shown in FIG. 9B. The anchoring mechanism can anchor the stylet in a particular location where re-entry is desired, i.e., can prevent proximal movement, and then can be dislodged as the stylet is advanced distally past the location.

Any of the stylets described herein can include a marker, such as a radiopaque marker, to help identify the location of the stylet in situ with imaging. For example, referring to the stylet 100 of FIGS. 1A-2C, the connector 106 between the proximal portion 101 and the middle portion 102 can form the radiopaque marker. In some embodiments, a radiopaque coating, such as platinum, can be applied to portions of the stylet 100.

Any of the stylets described herein can include a torquer configured to be tightened onto the stylet for rotational control. In some embodiments, the torquer can be aligned with a particular angle in the stylet. For example, the torquer can align with one or more of the angles of the s-curve 107 of the stylet 100.

Any of the stylets described herein can be sized and configured to fit within a guidewire channel of a catheter, such as through a guidewire channel of an occlusion-crossing device. Such exemplary occlusion-crossing devices are described in co-pending patent applications: U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1; U.S. patent application Ser. No. 13/433,049, titled "OCCLUSION-CROSSING DEVICES, IMAGING, AND ATHERECTOMY DEVICES," filed Mar. 28, 2012, Publication No. US-2012-0253186-A1; International Patent Application titled "OCCLUSION-CROSSING DEVICES," filed herewith; and International Patent Application titled "CHRONIC TOTAL OCCLUSION CROSSING DEVICES WITH IMAGING," filed herewith, all of which are incorporated by reference in their entireties.

Further, any of the stylets and/or catheters described herein can be oriented, directed, or steered using image guidance, such as optical coherence tomography, ultrasound, radiofrequency imaging, or fluoroscopy.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A stylet for re-entry into a vessel comprising:
   an elongate body having a proximal portion, a middle curved portion, a pointed distal end, and a longitudinal axis extending through the proximal portion, the middle curved portion, and the pointed distal end;
   wherein the proximal portion and the middle curved portion have substantially circular cross-sections, and wherein the middle curved portion has a pre-shaped curve along the longitudinal axis configured to match a curve of an occlusion-crossing device;
   wherein the pointed distal end has an s-shaped curve along the longitudinal axis and a flattened portion along the longitudinal axis, the flattened portion having a substantially oblong cross-section; and wherein the flattened portion tapers to a sharp tip at the pointed distal end.

2. The stylet of claim 1, wherein the s-shaped curve is within the flattened portion.

3. The stylet of claim 1, wherein at least one of the distal end or the middle curved portion comprises nitinol.

4. The stylet of claim 1, wherein the proximal portion comprises stainless steel.

5. The stylet of claim 1, wherein the pre-shaped curve forms an angle of 130 to 170 degrees.

6. The stylet of claim 5, wherein the angle is approximately 150 degrees.

7. The stylet of claim 1, wherein the s-shaped curve has two curves, the first curve forming a first angle of 120 to 160 degrees and the second curve forming an angle of 120 to 160 degrees.

8. The stylet of claim 1, wherein the s-shaped curve has a first curve and a second curve, the second curve distal to the first curve, and wherein the pre-shaped curve is aligned in substantially the same direction as the second curve.

9. The stylet of claim 1, wherein the pointed distal end includes an anchor.

10. The stylet of claim 1, wherein the pointed distal end is configured to penetrate a vessel wall.

11. The stylet of claim 1, wherein the pointed distal end has the s-shaped curve when deployed from the occlusion-crossing device.

12. A method of re-entering a true lumen during occlusion-crossing comprising:
    orienting a distal end of a catheter having a bend therein towards the true lumen of a vessel;
    introducing a stylet through a guidewire channel of the catheter, the stylet comprising:
        an elongate body having a proximal portion, a middle curved portion, a pointed distal end, and a longitudinal axis extending through the proximal portion, the middle curved portion, and the pointed distal end,
        wherein the proximal portion and the middle curved portion have substantially circular cross-sections, and wherein the middle curved portion has a pre-shaped curve along the longitudinal axis configured to match a curve of an occlusion-crossing device,
        wherein the pointed distal end has an s-shaped curve along the longitudinal axis and a flattened portion along the longitudinal axis, the flattened portion having a substantially oblong cross-section,
        wherein the flattened portion tapers to a sharp tip at the pointed distal end, and
        wherein inserting the stylet comprises inserting until the curved middle portion of the stylet aligns with the bend in the catheter and the pointed distal end of the stylet extends out of a distal end of the catheter; and
    advancing the stylet such that the pointed distal end pierces through a wall of the vessel; and
    directing the catheter over the stylet and into the true lumen of the vessel.

13. The method of claim 12, further comprising orienting the stylet within the catheter such that the pointed distal end of the stylet curves towards the vessel wall before advancing the stylet.

14. The method of claim 12, further comprising reorienting the catheter within the true lumen after directing the catheter over the stylet.

15. The method of claim 12, wherein reorienting the catheter comprises reorienting without puncturing an opposite vessel wall.

16. The method of claim 12, further comprising determining an orientation of the stylet based upon an alignment of the curved middle portion with the bend in the catheter.

17. The method of claim 12, further comprising using image guidance to orient the catheter.

* * * * *